(12) United States Patent
Boctor et al.

(10) Patent No.: US 12,133,818 B2
(45) Date of Patent: Nov. 5, 2024

(54) PROVIDING SENSORY STIMULATIONS VIA PHOTOACOUSTIC, PIEZO-BASED, THERMAL, AND/OR ELECTRICAL EFFECTS

(71) Applicant: The Johns Hopkins University, Baltimore, MD (US)

(72) Inventors: Emad M. Boctor, Baltimore, MD (US); Peter Gehlbach, Monkton, MD (US); James Spicer, Baltimore, MD (US); Jeeun Kang, Baltimore, MD (US); Maged Harraz, Ellicott City, MD (US)

(73) Assignee: The Johns Hopkins University, Baltimore, MD (US)

( * ) Notice: Subject to any disclaimer, the term of this patent is extended or adjusted under 35 U.S.C. 154(b) by 1394 days.

(21) Appl. No.: 16/612,257

(22) PCT Filed: May 10, 2018

(86) PCT No.: PCT/US2018/032113
§ 371 (c)(1),
(2) Date: Nov. 8, 2019

(87) PCT Pub. No.: WO2018/209118
PCT Pub. Date: Nov. 15, 2018

(65) Prior Publication Data
US 2023/0100414 A1    Mar. 30, 2023

Related U.S. Application Data

(60) Provisional application No. 62/504,351, filed on May 10, 2017.

(51) Int. Cl.
*A61F 9/08*    (2006.01)
*A61N 7/00*    (2006.01)

(52) U.S. Cl.
CPC .............. *A61F 9/08* (2013.01); *A61N 7/00* (2013.01); *A61N 2007/0026* (2013.01)

(58) Field of Classification Search
CPC .................... A61F 9/08; A61N 2007/0026
(Continued)

(56) References Cited

U.S. PATENT DOCUMENTS

| 2006/0146284 | A1* | 7/2006 | Collins | ............... A61B 3/1208 351/215 |
| 2008/0015553 | A1 | 1/2008 | Zacharias | |

(Continued)

FOREIGN PATENT DOCUMENTS

| JP | 2014-054463 A | 3/2014 | |
| WO | WO-2016070134 A1 * | 5/2016 | ............. A61B 18/12 |

OTHER PUBLICATIONS

International Search Report for Application No. PCT/US2018/032113, mailed on Nov. 7, 2018, 12 pages.

*Primary Examiner* — Nicole F Lavert
*Assistant Examiner* — Nicole F Johnson
(74) *Attorney, Agent, or Firm* — Harrity & Harrity, LLP

(57) ABSTRACT

A device may include an image capturing component to obtain images of an environment of a user, and a light projection system. The light projection system may include a laser source and an optical imager. The device may process, in real-time, images captured by the image capturing component to derive signals for controlling the laser source, provide the signals to the laser source to enable the laser source to generate a laser beam pattern, cause the optical imager to raster scan the laser beam pattern to an absorptive element. The absorptive element may be disposed on or in the user, and positioned proximate to a region-of interest, of the user, that includes neuronal cells. The laser beam pattern may cause the absorptive element to produce acoustic energy that cause depolarization of the (Continued)

neuronal cells. The sensory stimulation may enable the user to visually and/or auditorily perceive the environment.

20 Claims, 24 Drawing Sheets

(58) Field of Classification Search
USPC .......................................................... 607/54
See application file for complete search history.

(56) References Cited

U.S. PATENT DOCUMENTS

| | | | |
|---|---|---|---|
| 2008/0077196 A1* | 3/2008 | Greenberg | A61N 1/0543 607/54 |
| 2010/0198081 A1* | 8/2010 | Hanlin | A61B 5/02007 600/478 |
| 2014/0300798 A1* | 10/2014 | Sapir | G02B 27/146 348/345 |
| 2015/0238362 A1* | 8/2015 | Chayet | A61F 9/08 348/63 |
| 2016/0022976 A1 | 1/2016 | Peyman | |
| 2017/0363871 A1* | 12/2017 | Vallius | G02B 6/0016 |

* cited by examiner

PROVIDING SENSORY STIMULATIONS VIA PHOTOACOUSTIC, PIEZO-BASED, THERMAL, AND/OR ELECTRICAL EFFECTS

CROSS-REFERENCE TO RELATED APPLICATIONS

This application is a 371 national stage of PCT Application No. PCT/US2018/032113 filed on May 10, 2018, entitled "PROVIDING SENSORY STIMULATIONS VIA PHOTOACOUSTIC, PIEZO-BASED, THERMAL, AND/OR ELECTRICAL EFFECTS," which claims priority to U.S. Provisional Patent Application No. 62/504,351 filed on May 10, 2017, entitled "PROSTHETIC EYE," all of which are incorporated by reference herein.

BACKGROUND

A large population of the world is visually impaired. Visual impairment includes conditions such as blindness (including monocular blindness) and poor or low vision. Leading causes of blindness include glaucoma, macular degeneration, cataract development, diabetic retinopathy, and retinitis pigmentosa. In some cases, patients who suffer from blindness preserve some retinal function.

SUMMARY

According to some implementations, a method may include obtaining information relating to an environment of a user, processing the information to derive one or more signals representative of the information, generating a light-based pattern based on the one or more signals, and outputting the light-based pattern after generating the light-based pattern. The light-based pattern may be directed at an absorptive element. The absorptive element may be disposed on or in the user, and positioned proximate to a region-of-interest, of the user, that includes neuronal cells. The light-based pattern may cause the absorptive element to produce acoustic energy that causes depolarization of the neuronal cells in a controlled spatiotemporal resolution in the region-of-interest. The depolarization of the neuronal cells may enable the user to visually and/or auditorily perceive the environment, be alleviated from pain, and/or be manipulated to perform a movement of a body part of the user.

According to some implementations, a device may include an image capturing component to obtain images of an environment of a user, and a light projection system. The light projection system may include a laser source and an optical imager. The device may include one or more memories, and one or more processors, communicatively coupled to the one or more memories, to process, in real-time, images captured by the image capturing component to derive signals for controlling the laser source, provide the signals to the laser source to enable the laser source to generate a laser beam pattern, cause the optical imager to raster scan the laser beam pattern to an absorptive element. The absorptive element may be disposed on or in the user, and positioned proximate to a region-of-interest, of the user, that includes neuronal cells. The laser beam pattern may cause the absorptive element to produce acoustic energy that causes depolarization of the neuronal cells in a controlled spatiotemporal resolution in the region-of-interest. The depolarization of the neuronal cells may enable the user to visually and/or auditorily perceive the environment, be alleviated from pain, and/or be manipulated to perform a movement of a body part of the user.

According to some implementations, a non-transitory computer-readable medium may store instructions. The instructions may include one or more instructions that, when executed by one or more processors, cause the one or more processors to obtain information relating to an environment of a user, process the information to derive one or more signals representative of the information, generate a light-based pattern based on the one or more signals, and output the light-based pattern after generating the light-based pattern. The light-based pattern may be directed at an absorptive component. The absorptive component may include a first absorptive layer, a second absorptive layer, and a piezoelectric array disposed between the first absorptive layer and the second absorptive layer. The absorptive component may be positioned proximate to a region-of-interest, of the user, associated with neuronal cells. The light-based pattern may enable the first absorptive layer and the second absorptive layer to produce acoustic energy that activates the piezoelectric array to cause depolarization of the neuronal cells in a controlled spatiotemporal resolution in the region-of-interest. The depolarization of the neuronal cells may enable the user to visually and/or auditorily perceive the environment, be alleviated from pain, and/or be manipulated to perform a movement of a body part of the user.

DETAILED DESCRIPTION

Figure 1A:
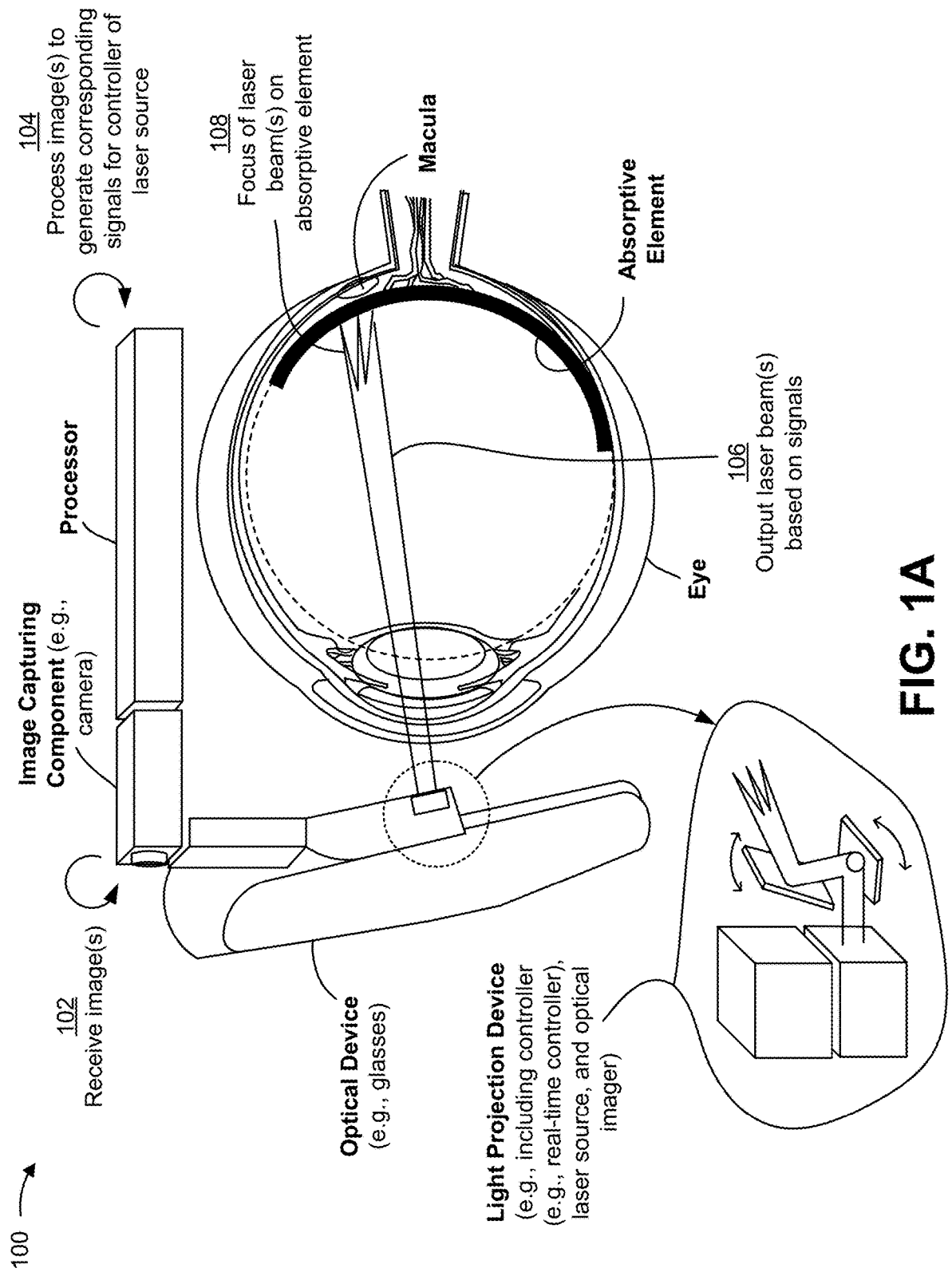
FIGS. 1A-1S are diagrams of an example implementation described herein.

The following detailed description of example implementations refers to the accompanying drawings. The same reference numbers in different drawings may identify the same or similar elements.

People who suffer from retinitis pigmentosa have a degenerate outer retina (e.g., damaged retinal photoreceptors), but an inner retina that is intact and capable of sending signals to the visual cortex, and the frontal cortex, of the brain via the optic nerve. Present treatments for this condition include embedding electrodes into the inner retinal tissue, and encoding images to create electrical signals for stimulating ganglion cell axons in the retinal tissue to assist with vision. However, this provides a limited level of vision (e.g., only about 64 static pixels of information). In addition, it takes a long time for the brain to adjust to such stimulations, and, as a result, many patients tend to abandon the treatment by turning off the electrodes. Other treatments for the condition include implanting retinal prosthesis electrode arrays to provide electrical current stimulation, and implanting sub-retinal photodiode arrays to provide electrical current stimulation via pulsed infrared light. However, implanting such stimulators in the retinal space requires a high level of surgical skill and risks permanent damage to retinal neurons. Stabilization of the implant, to permit proper function during vigorous rotational movements of the eye, also poses a challenge. Furthermore, such treatments are constrained by the implant hardware design—i.e., which require a fixed quantity of electrodes in the array—and are thus not adaptable for different users.

Some implementations, described herein, provide a photoacoustic-based stimulation system that is capable of stimulating neurons (or neuronal cells) using photoacoustic effects. In some implementations, the photoacoustic-based stimulation system is capable of directing light (e.g., a near-infrared laser light) at a photoacoustic sensitive element or absorptive element or layer, disposed proximate to the neuronal cells, to generate highly localized acoustic energy (e.g., ultrasound waves). The acoustic energy causes an increase in cellular adenosine triphosphate (ATP) consumption and induces depolarization of the neuronal cells (via thermal expansion of the absorptive element (e.g., gradual transient of thermal energy)), resulting in neural modulation. In some implementations, the photoacoustic-based stimulation system includes an image capturing component (e.g., including one or more cameras) configured to capture images, one or more processors configured to process the captured images, and an external or intra-cavity light projection system that includes a near-infrared laser source, a processor (e.g., a real-time, or near real-time, controller) configured to cause the near-infrared laser source to output laser light pulses based on the processed images, and an optical imager configured to direct the light pulses at the absorptive element to generate acoustic energy. The photoacoustic-based stimulation system is capable of being adapted for use with any type of neuronal cell relating to brain function, such as, for example, neuronal cells associated with vision or hearing. Thus, in any case, a biocompatible, light absorptive element may be disposed proximate, or adjacent, to a region-of-interest (e.g., tissue and/or the like) for stimulation, and excited with light energy (e.g., at appropriate wavelength(s) (e.g., selected by considering light penetration and mechanical energy and/or thermal energy needed for appropriate stimulation)) so as to cause mechanical energy and/or thermal energy to be generated. In a case where the photoacoustic-based stimulation system is adapted for use with a user's retinal cells, the photoacoustic-based stimulation system is capable of providing virtual vision to the user (e.g., where, even in situations where light perceiving cones and rods may be damaged, light transduction on the user's ocular system causes bipolar cells and ganglion cells to become depolarized, thus permitting visual information to be transferred through the user's optic nerve). Some implementations, described herein, further provide a visual cortex monitoring system that is capable of monitoring (and/or recording) brain activities resulting from photoacoustic-based stimulation, and providing closed-loop feedback that enables the photoacoustic-based stimulation system to calibrate photo acoustic-based stimulation parameters and adaptively operate for individual users.

In this way, the system(s) enable enhanced stimulation resolution and deeper penetration of neuronal cells, thus providing more effective virtual sensory functionality for users. For example, excitation of an absorptive element and/or the like (e.g., to cause thermal stimulation and/or vaporization-based stimulation of neuronal cells) can result in depolarization of neuronal cells in controlled spatiotemporal resolution, providing sensory perception to a user such that the user may visually and/or auditorily perceive an environment, be alleviated from pain (e.g., from disease and/or the like) (e.g., via inhibition(s) to C-fiber nerves), become manipulated to perform motor function(s) (e.g., via muscle nerve and/or motor cortex stimulation), and/or the like. In cases where system implementations described herein are applied to a user's retinal neurons, for example, the user can experience improved virtual vision—e.g., fast and fine resolution of vision, such as that at greater than 64 static pixels of information. In addition, non-invasive, and compact, system implementations described herein reduce or eliminate a need for patients to undergo sensory-related implant surgeries (e.g., to a retina and/or the like), thereby reducing treatment costs and improving user safety. Furthermore, the use of a laser-based photoacoustic-based stimulation system (that leverages laser light) permits fine control of light pulse durations and targeting of light energy, which provides a high degree of operative flexibility. Moreover, closed-loop feedback, provided by the visual cortex monitoring system, also enables adaptive stimulation (e.g., for users with different ocular anatomies), which maximizes the performance of the photoacoustic-based stimulation system, and improves user safety.

Figure 1B:
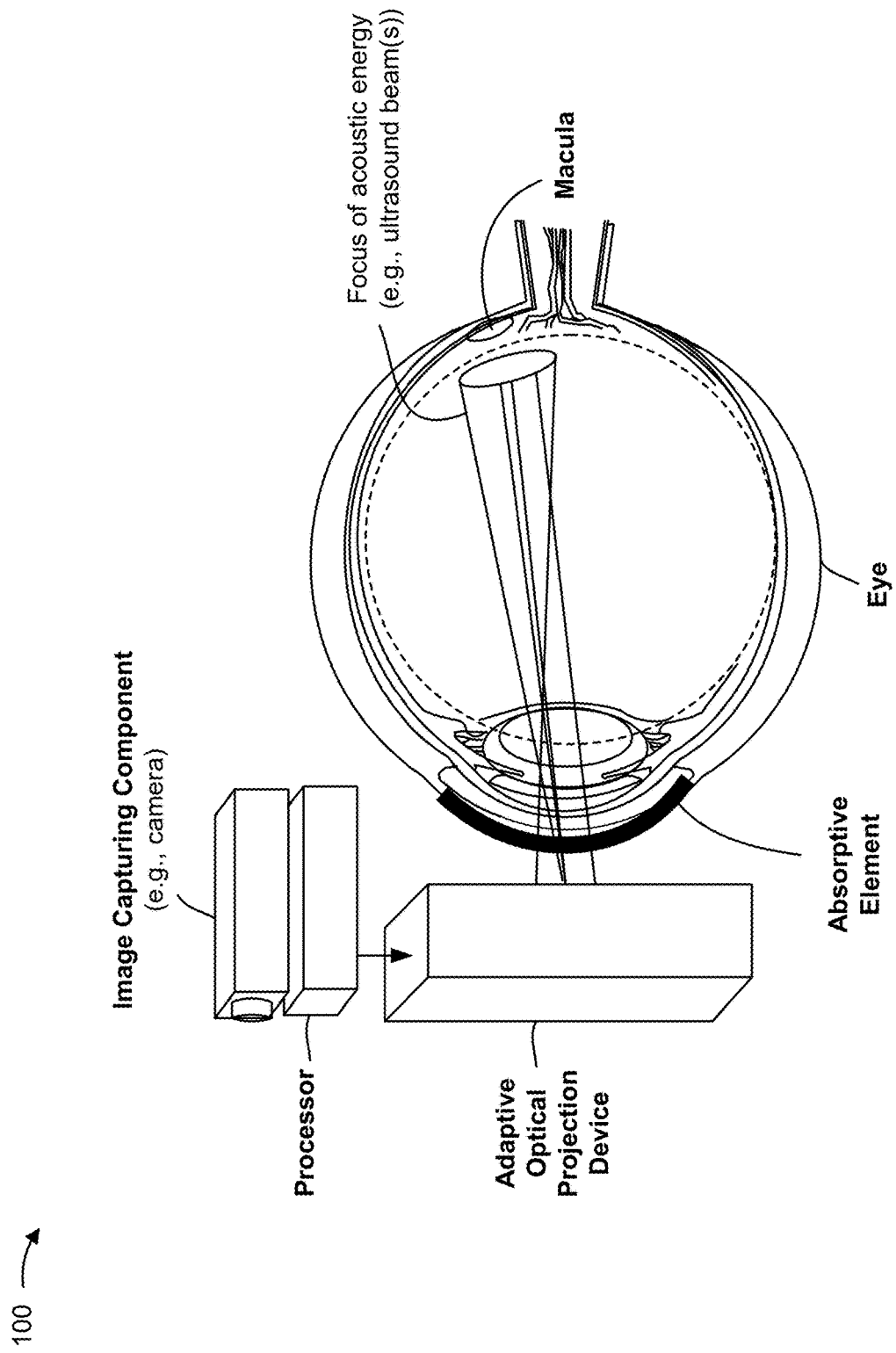
Figure 1C:
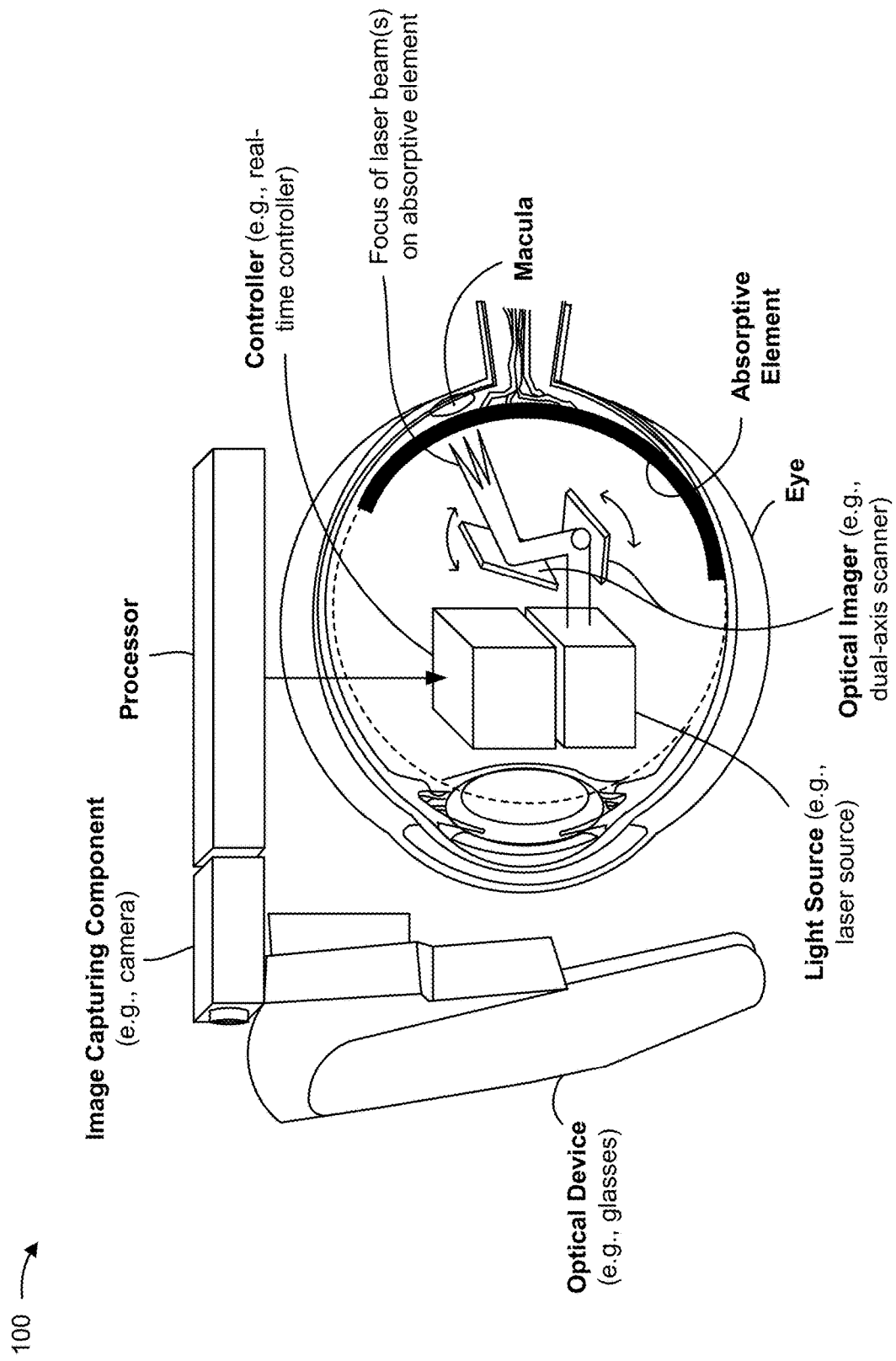
Figure 1D:
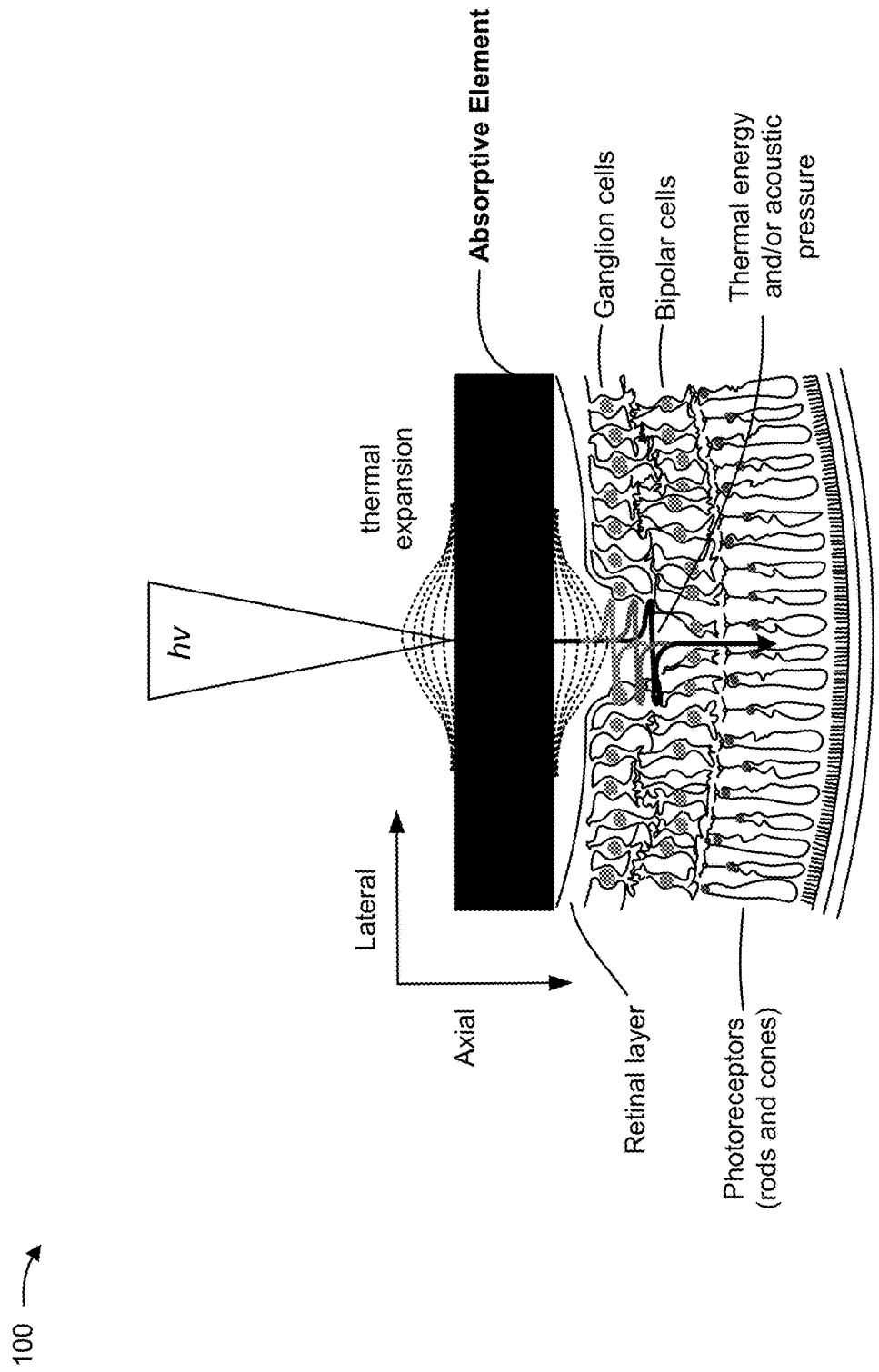
Figure 1E:
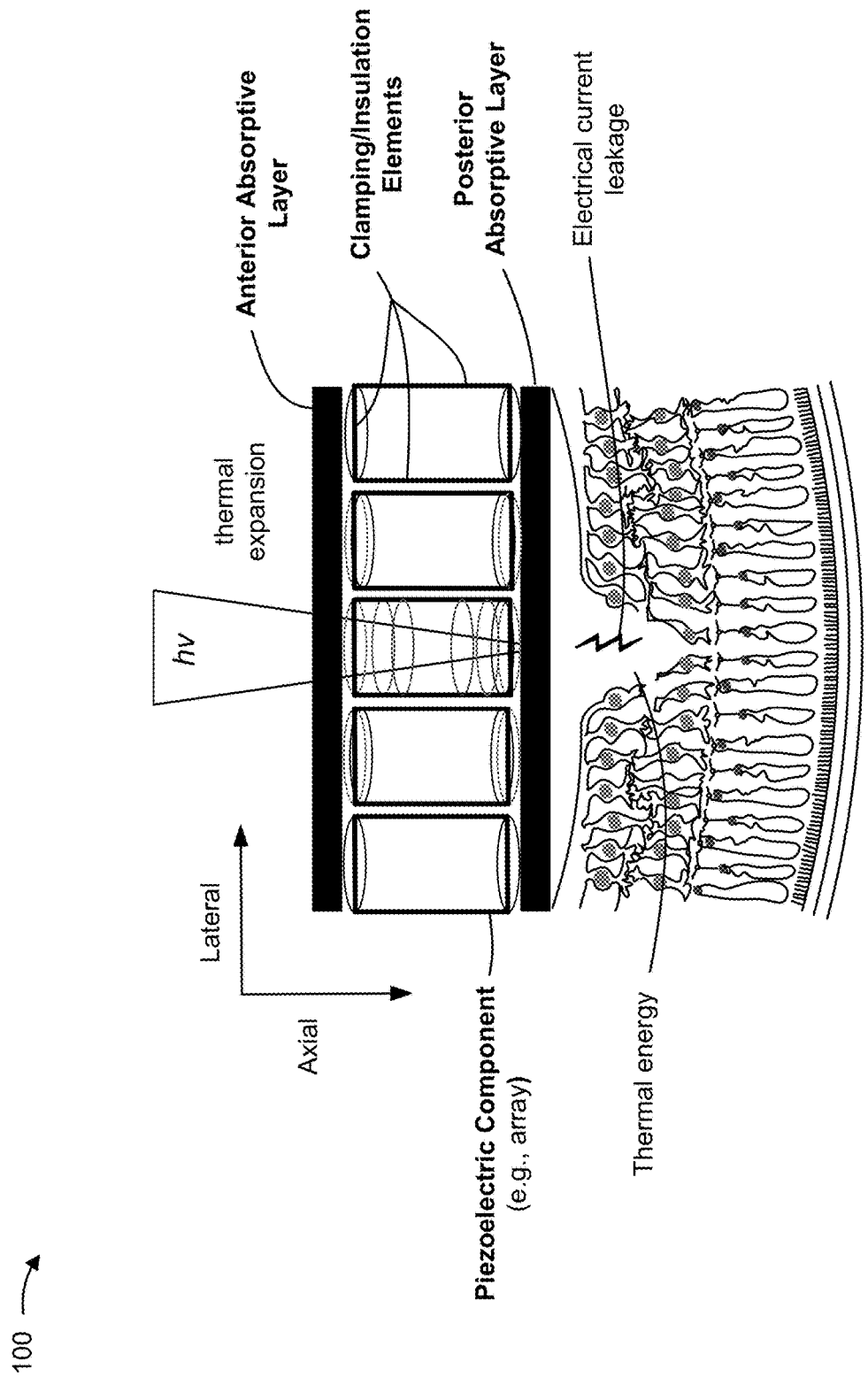
Figure 1F:
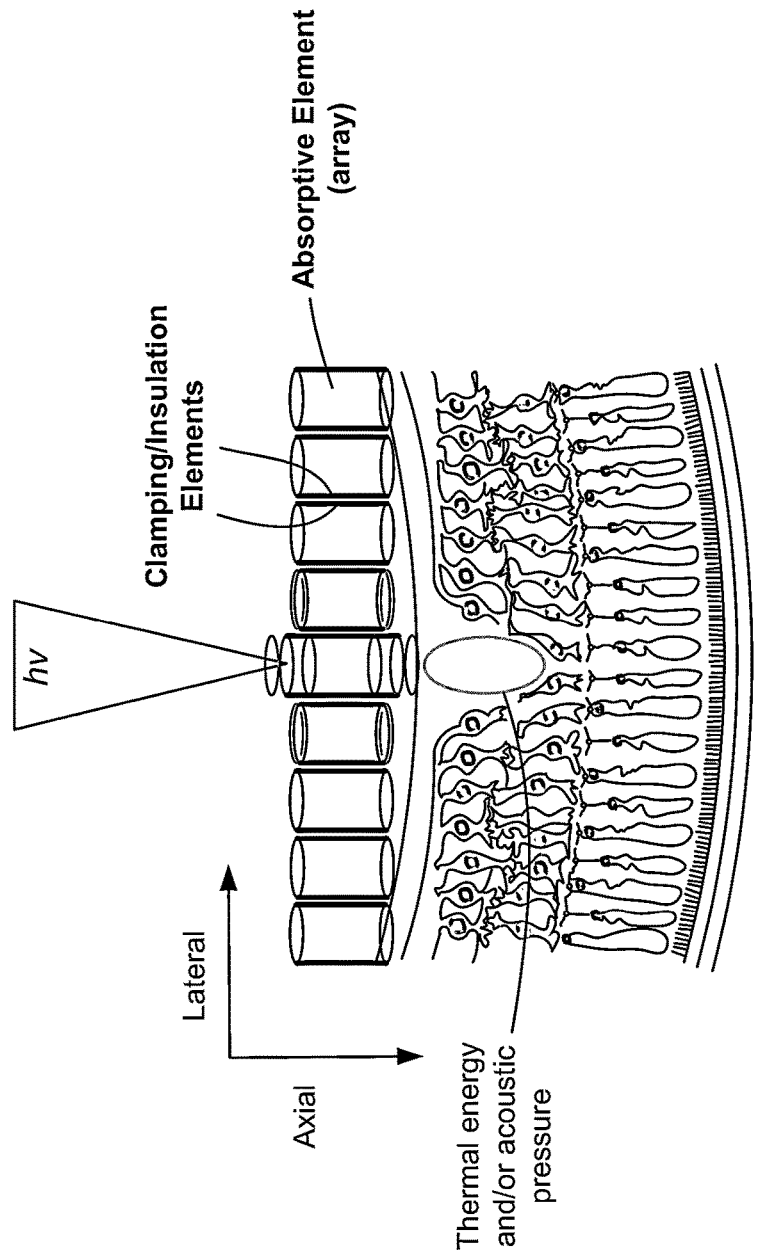
Figure 1G:
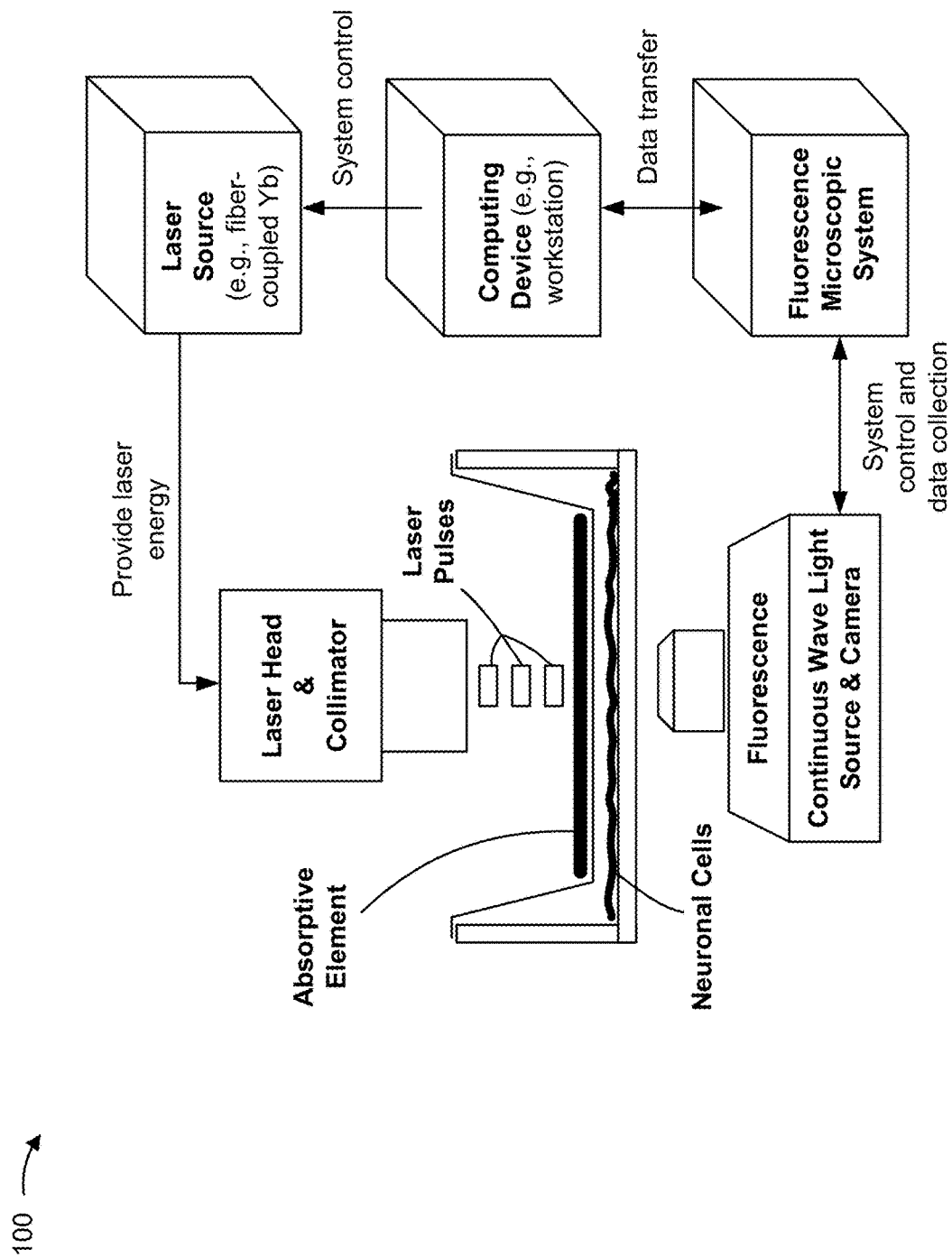
Figure 1H:
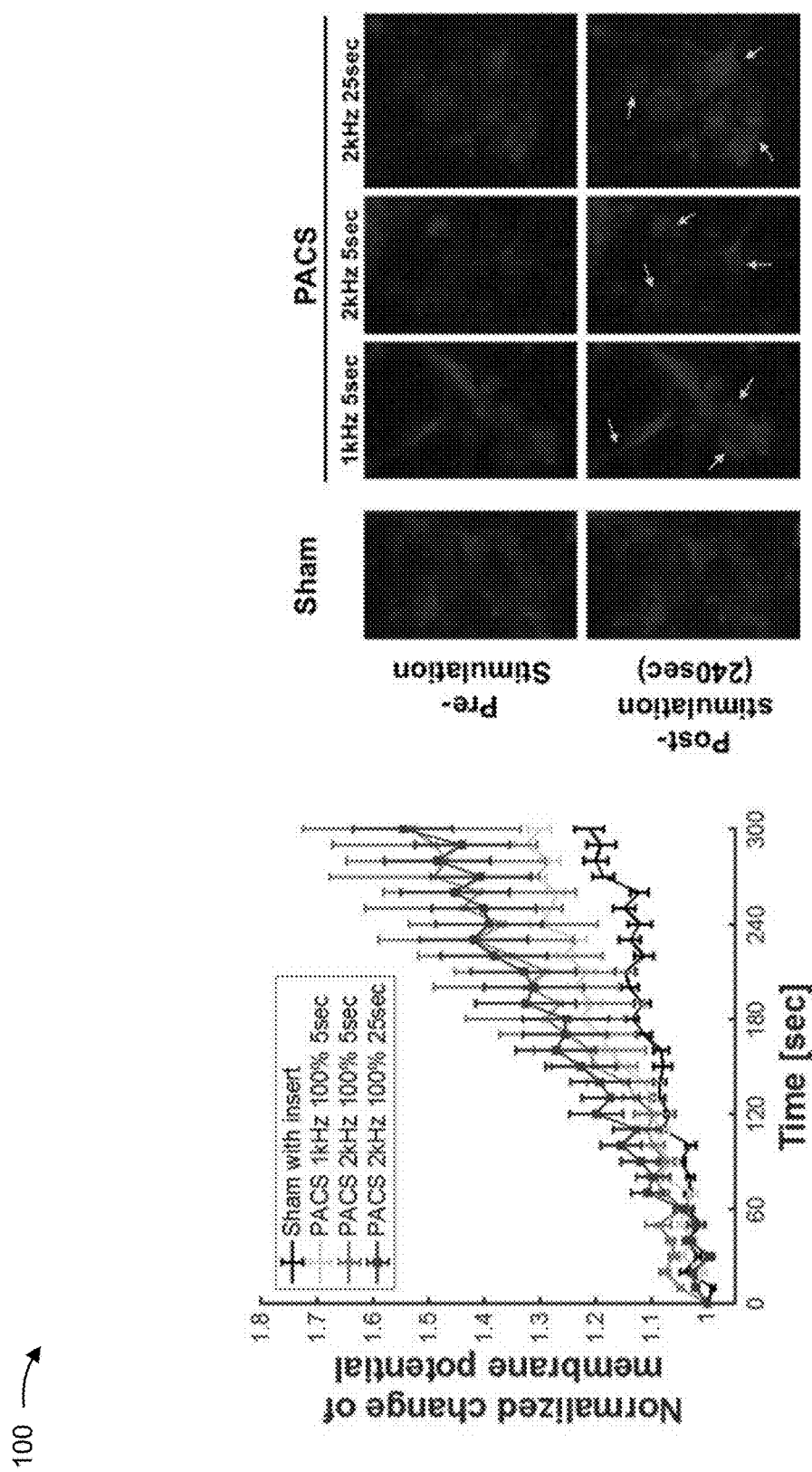
Figure 1I:
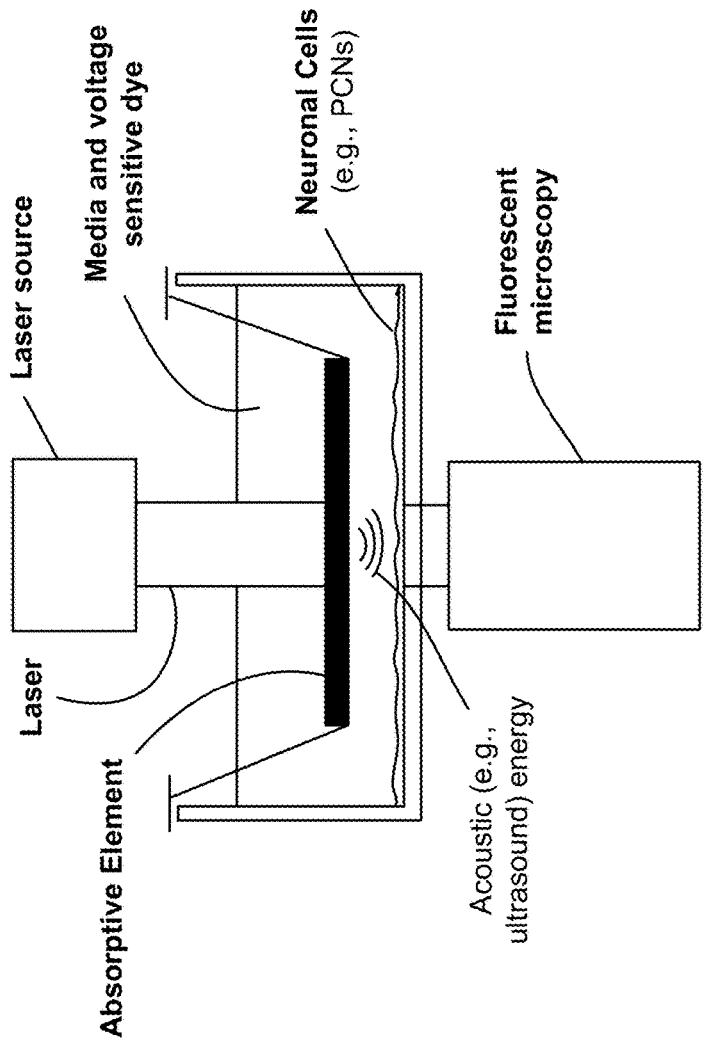
Figure 1J:
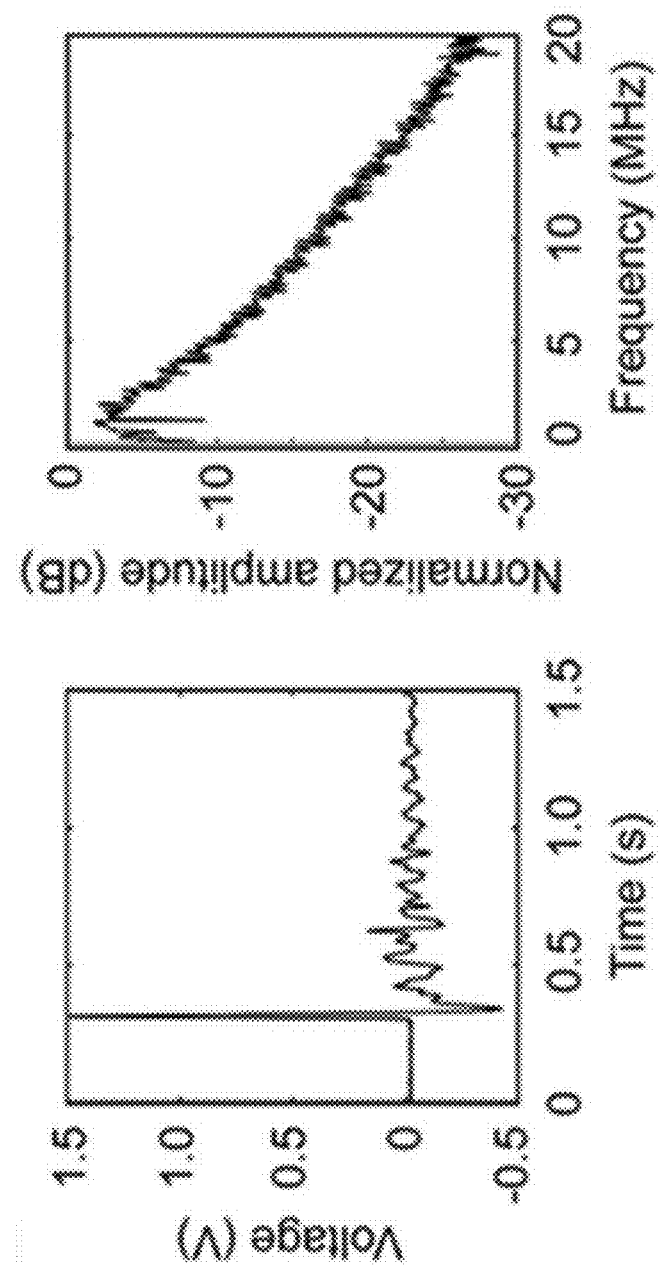
Figure 1K:
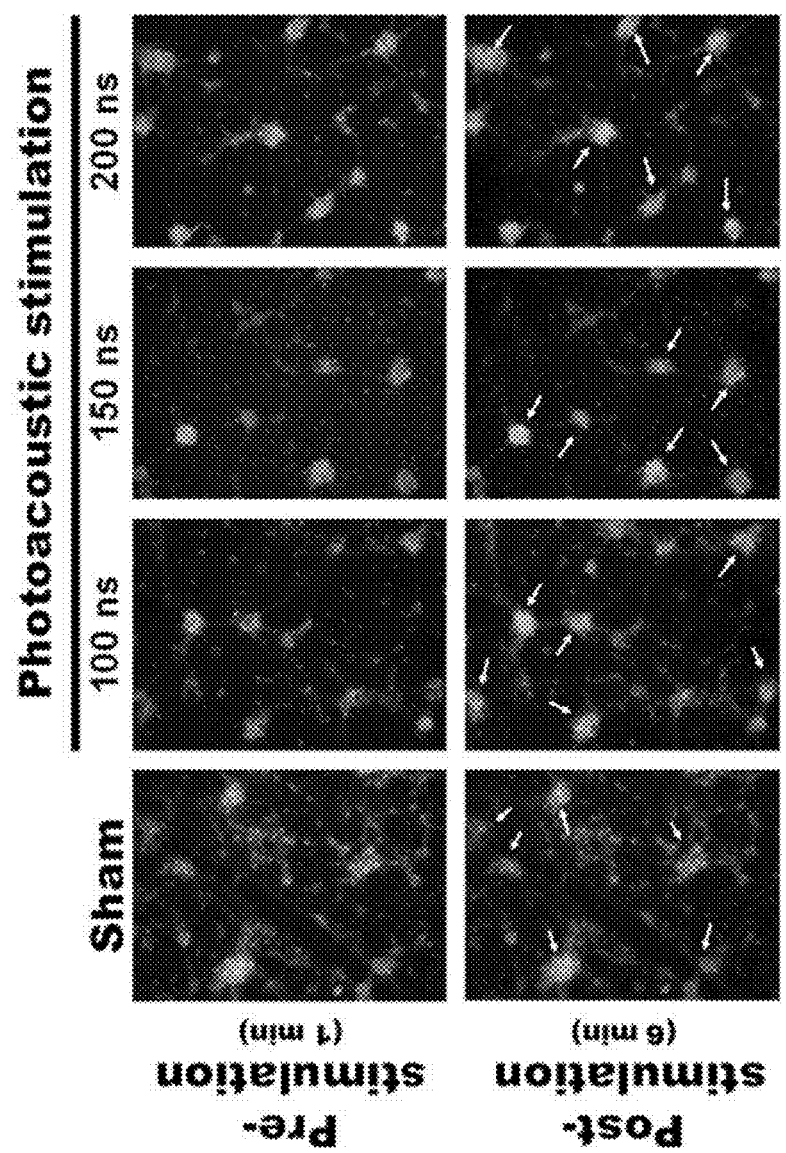
Figure 1L:
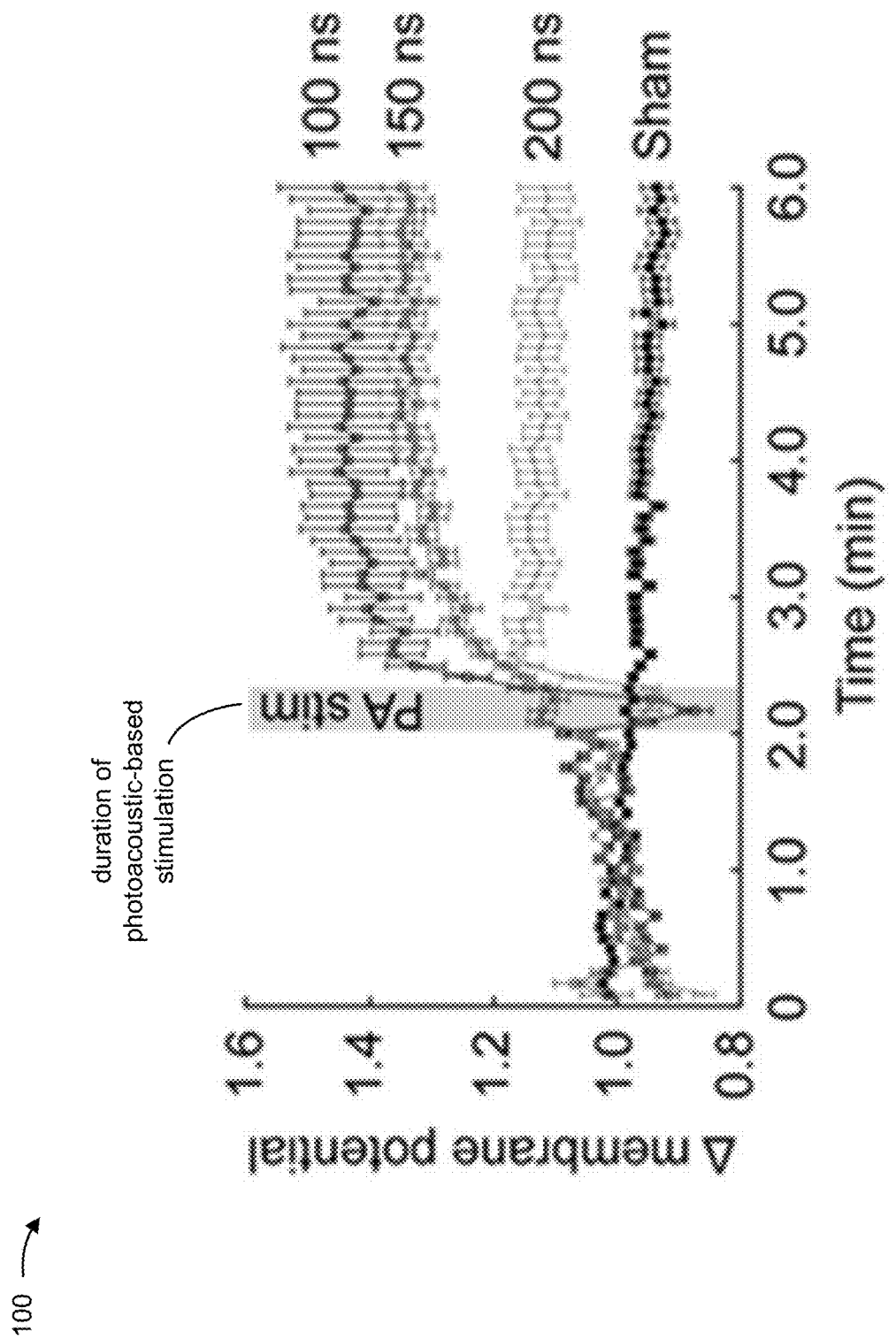
Figure 1M:
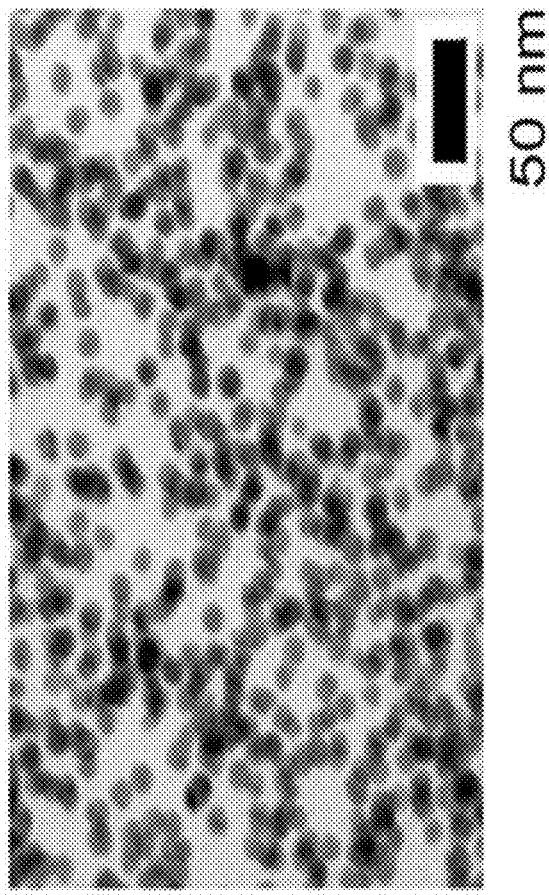
Figure 1N:
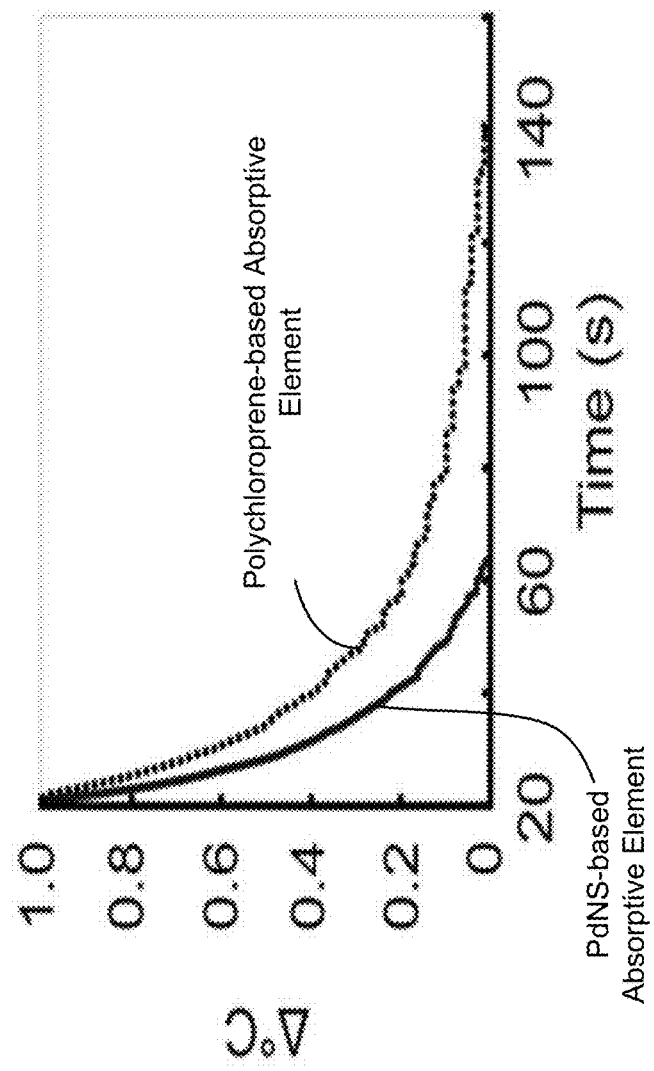
Figure 10:
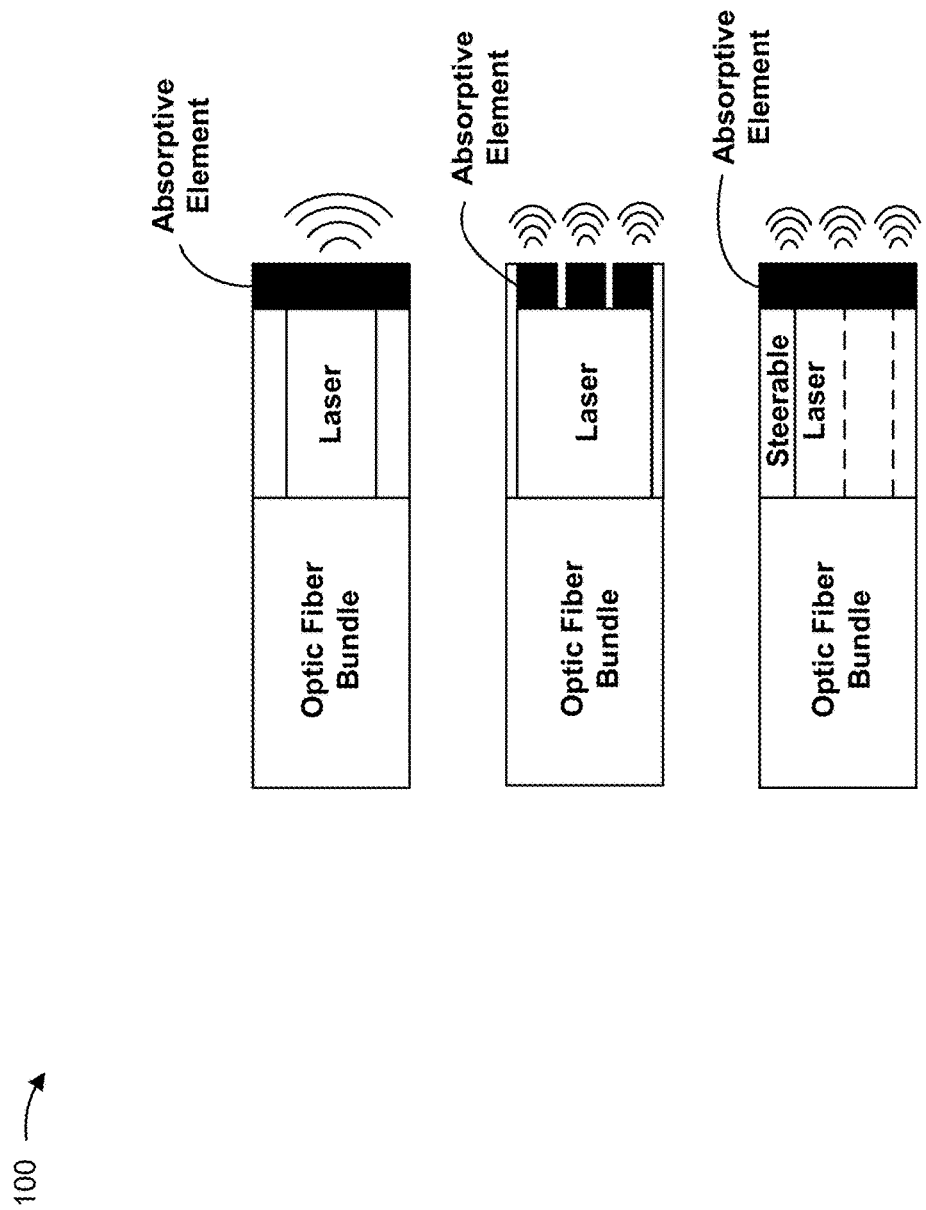
Figure 1P:
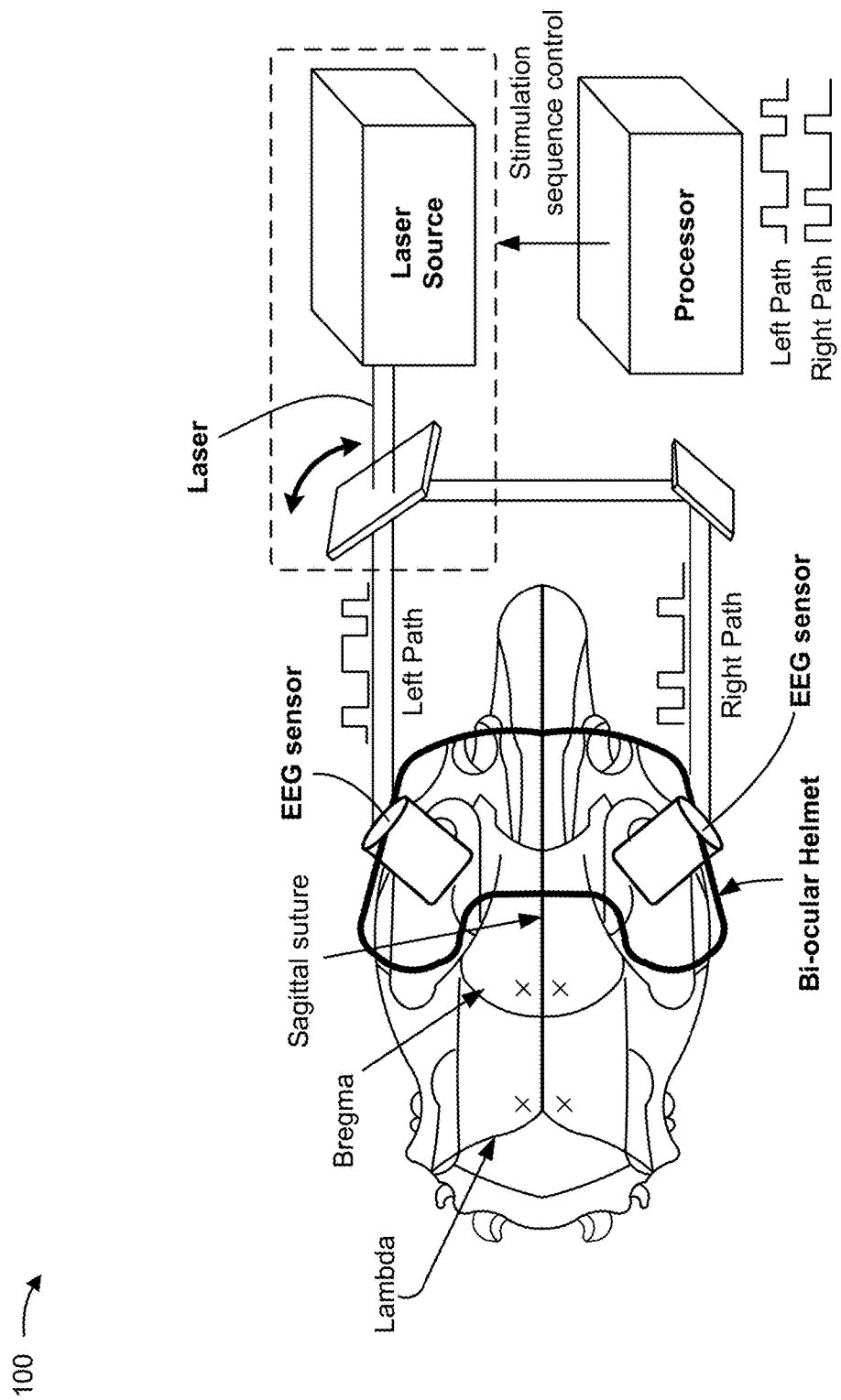
Figure 1Q:
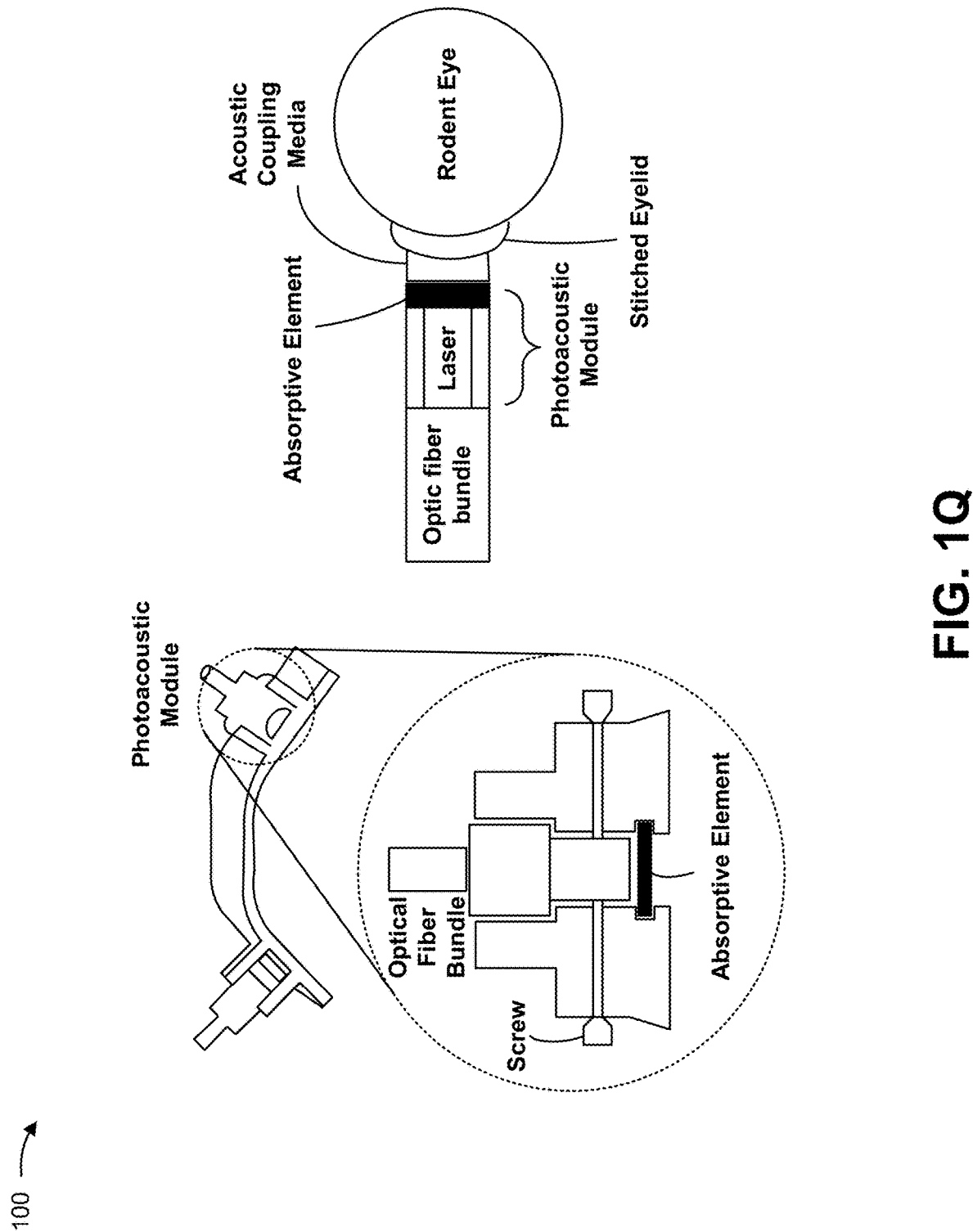
Figure 1R:
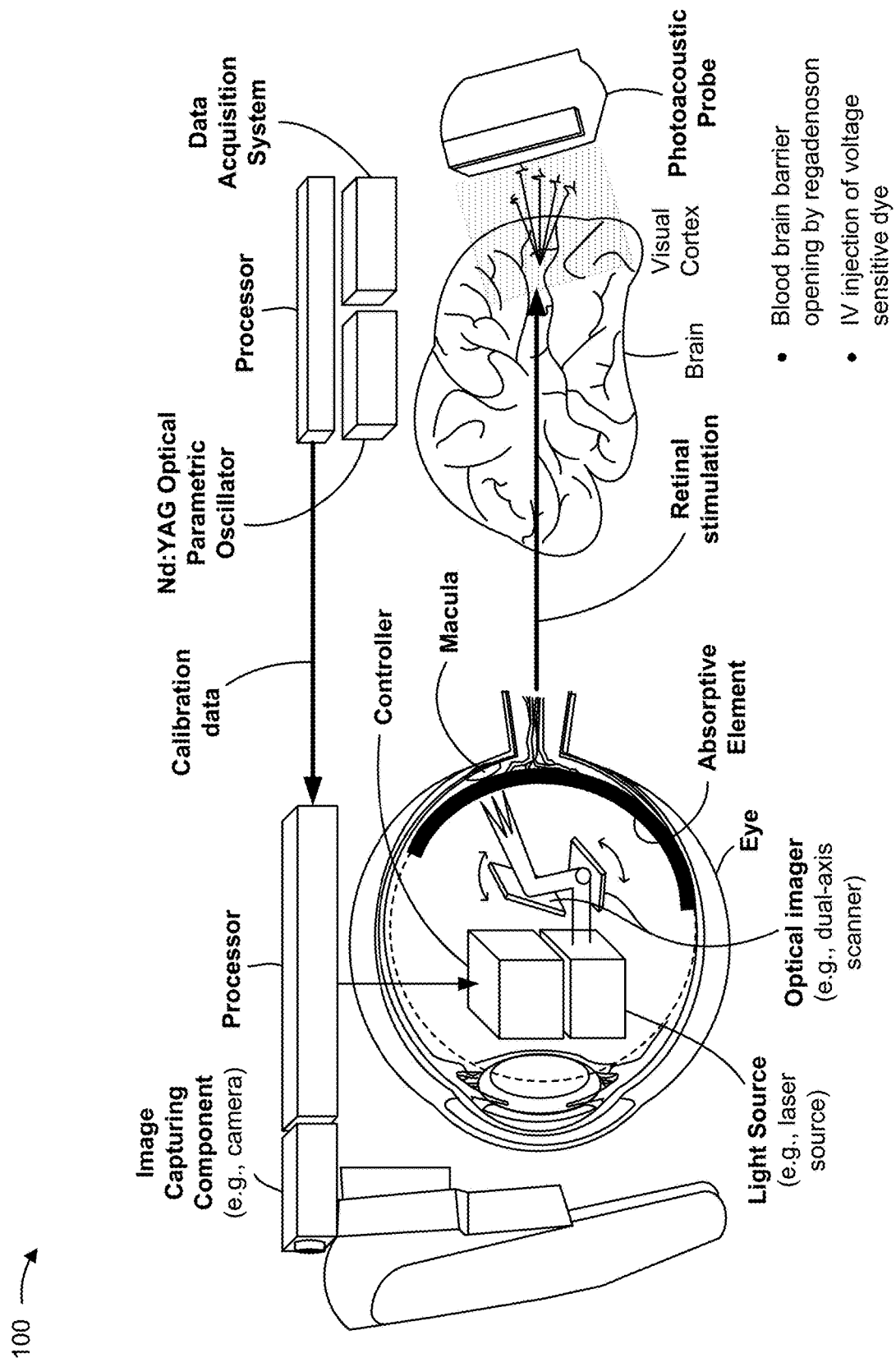
Figure 1S:
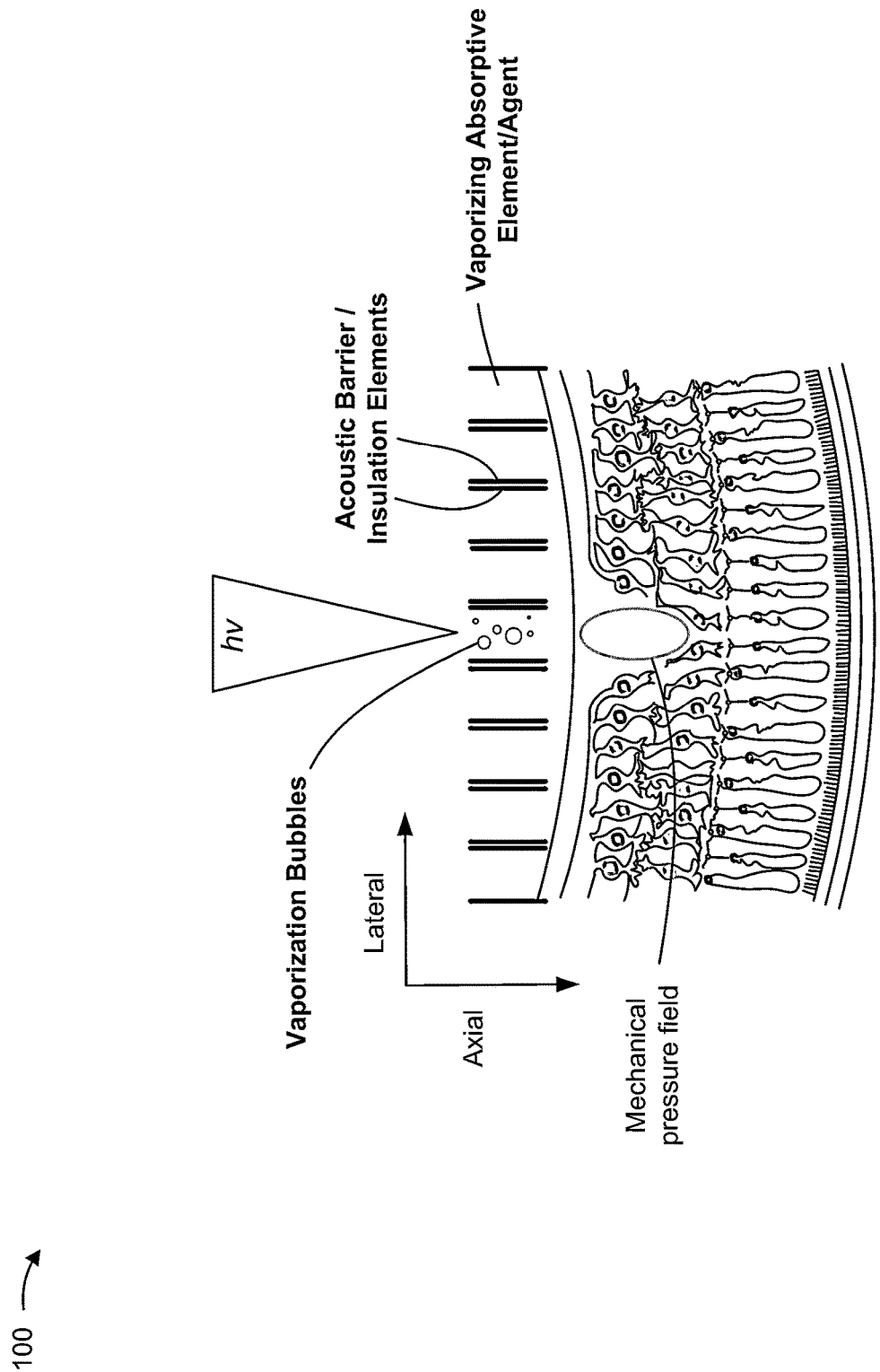

FIGS. 1A-1S are diagrams of an example implementation 100 described herein. As shown in FIG. 1A, example implementation 100 may include a photoacoustic-based stimulation system that includes an image capturing component (e.g., one or more cameras), a processor, a light projection device, and absorptive element. As shown, the photoacoustic-based stimulation system may be disposed entirely outside of a user's (e.g., a patient's) eye, and may be coupled to, or integrated with, an optical device, such as a pair of glasses. In some implementations, the photoacoustic-based stimulation system may include a power source (e.g., one or more batteries) that provides power for the various components of the photoacoustic-based stimulation system.

The image capturing component may be configured to capture live images of an environment of a user. The processor may (e.g., based on one or more instructions) be configured to process images captured by the image capturing component, such as by performing intensity truncation, coordination conversion (e.g., including converting between coordinate systems, such as via warping and/or the like), and providing control signals, based on the processed images, to the light projection device in real-time (or near real-time).

The light projection device may include a controller (e.g., a real-time controller) communicatively coupled to the processor, a laser source communicatively coupled to the controller, and an optical imager or scanner. In some implementations, the laser source may provide pulsed (e.g., non-injurious) light energy into a patient's eye, through a biological lens of the patient's eye, based on commands provided by the controller. In some implementations, the optical imager may include one or more mirrors (e.g., a dual-axis scanner) configured to permit raster scanning, and directing, of light from the laser source, to the absorptive element. For example, the optical imager may include one or more miniaturized galvo-mirrors, microelectromechanical system (MEMS) actuators, and/or the like.

The absorptive element may include one or more biocompatible materials configured to absorb laser energy and generate acoustic signals (e.g., ultrasound signals or beams and/or the like) based on the laser energy. In some implementations, the materials may exhibit high light absorbance characteristics and high thermal durability. Various examples of absorptive element configurations are described in more detail below in connection with FIGS. 1D-1F and 1S.

As shown in FIG. 1A, the absorptive element may be disposed over a portion of a retina within a cavity of a patient's eye. In some implementations, the absorptive element may be surgically coupled to retinal tissue. In some implementations, any needed preparations within the cavity of the patient's eye, may also be made so as to permit laser light to enter the eye. In some implementations, the absorptive element may be disposed externally from a patient's eye (e.g., described in more detail below in connection with FIG. 1B).

As shown in FIG. 1A, and as shown by reference number 102, the image capturing component may receive image(s). As shown by reference number 104, the processor may process the image(s) to generate corresponding signals for controlling the laser source. In some implementations, the signals may include quantized visual information, such as geometry information, intensity information, and/or the like. In some implementations, the processor may provide the signals to the controller, which may, in turn, direct the laser source to output appropriate laser beam(s).

As shown by reference number 106, the laser source may output laser beam(s) based on the signals. As shown by reference number 108, the laser beam(s) may be focused on a portion, of the absorptive element, that is disposed adjacent, or proximate, to the patient's macula. In some implementations, the portion may have a diameter of a certain size (e.g., about 10 microns to 15 microns and/or the like) that permits high resolution imagery to be provided to the patient. In some implementations, pulse repetition frequency of the laser beam(s) (e.g., of about 1 kHz, 2 kHz, and/or the like) at a targeted location, and coupled with high raster speeds, may yield image resolutions of about 200 pixels by 200 pixels and/or the like.

Having various components of the photoacoustic-based stimulation system, such as the image capturing component, the processor, and the light projection device, disposed entirely outside of a patient's eye (e.g., as shown in FIG. 1A) provides a minimally invasive treatment option for the patient, which allows for more margin within the cavity of the patient's eye, and permits (e.g., continuous) thermal control, and flexible design, of the photoacoustic-based stimulation system.

As shown in FIG. 1B, and similarly to example implementation 100 of FIG. 1A, a photoacoustic-based stimulation system may include an image capturing component and a processor disposed outside of a cavity of a patient's eye. Although not shown, example implementation 100 of FIG. 1B may also include an optical device (e.g., glasses) to which various components of the photoacoustic-based stimulation system may be coupled or integrated. In contrast to example implementation 100 of FIG. 1A, here, an absorptive element may also be disposed outside of the cavity of the patient's eye—e.g., disposed over a portion (e.g., a biological lens portion) of the patient's eye.

As shown in FIG. 1B, the photoacoustic-based stimulation system may include an adaptive optical projector. In some implementations, the adaptive optical projector may include a controller and a laser source, similar to that described above in connection with example implementation 100 of FIG. 1A. Here, the adaptive optical projector may be configured to provide laser beam(s) in one or more predefined patterns—e.g., pulses, at distinct times and/or at distinct locations of the absorptive element, that cause the absorptive element to provide corresponding pattern(s) of acoustic (e.g., ultrasound) signals. In this way, aggregated acoustic beams may focus on a desired position within the cavity of the patient's eye (e.g., such as a portion, of the patient's retinal tissue, that is disposed adjacent, or proximate, to the patient's macula). Furthermore, the energy of each light pulse may provide a corresponding visual frame for a patient, which increases overall image frame rates, thereby providing improved virtual vision for the patient.

As shown in FIG. 1C, and similarly to example implementation 100 of FIG. 1A, a photoacoustic-based stimulation system may include an image capturing component and a processor disposed outside of a cavity of a patient's eye, and an absorptive element coupled to the retina of the patient's eye. However, in contrast to example implementation 100 of FIG. 1A, the light projection device—e.g., the controller and the optical imager—may also be disposed within the cavity of the patient's eye. In this case, the processor may provide signals (e.g., quantized visual information and/or the like) to the controller (e.g., wirelessly and/or via one or more wires—not shown), which may, in turn, cause the laser source to output corresponding laser beam(s), and cause the optical imager to direct the laser beam(s) at a portion, of the absorptive element, that is disposed adjacent, or proximate, to the patient's macula.

In some implementations, the photoacoustic-based stimulation system (e.g., one or more of the photoacoustic-based stimulation system implementations described above in connection with FIGS. 1A-1C) may be configured to stabilize, or ensure, optical alignment of the laser beam(s), the optical imager, and/or a target location within the patient's eye (e.g., the portion, of the absorptive element, that is disposed adjacent, or proximate, to the patient's macula) in an event of an offset in alignment (e.g., due to changes in orientation of the glasses and/or the like relative to the patient's eye). In some implementations, the photoacoustic-based stimulation system may stabilize the optical alignment by adjusting the optical imager (e.g., by adjusting an orientation of one or more mirrors in a dual-axis mirror configuration) based on information contained in images captured by the image capturing component. Additionally, or alternatively, and in some implementations, the photoacoustic-based stimulation system may include, or be associated with one or more motion sensors (e.g., accelerometer(s), gyroscope(s), and/or the like), and may obtain sensor data from the motion sensor(s), and utilize the sensor data to stabilize the optical alignment. In either case, the photoacoustic-based stimulation system may be capable of stabilizing the optical alignment without a need for user intervention.

In some implementations, a single, wide pulsed laser beam (e.g., in the millimeter range), or a large light-emitting diode (LED) source, flash lamp, and/or the like, may be provided through a programmable spatial light modulator—e.g., programmable based on real-time image data—and outputted via a dynamic diffraction map or pattern. Light through such a diffraction pattern (e.g., adjacent, or proximate, to an absorptive element) may produce a visual projection that closely mimics the real-time image data. Acoustic effects produced, in response to absorption of this light by the absorptive element, may provide enhanced virtual vision to a patient.

In various implementations, stimulus on neuronal cells may be conducted via light energy excitation controlled in a spatiotemporal domain. Stimulation mechanisms may include mechanical stimulus and thermal stimulus. Because photoacoustics is based on instantaneous thermal energy, synergy of mechanical and thermal stimulus may be controllable using optimized light excitations. In mechanical stimulus, for example, light-induced instantaneous thermal transient from an absorptive layer (e.g., an epiretinal absorptive layer) may produce acoustic energy (e.g., ultrasound waves) followed by thermoelastic expansion of the irradiated volume, leading to depolarization of target neuronal cells (e.g., an underlying retinal layer). In some implementations, mechanical energy may alternatively be obtained (e.g., rather than via thermoelastic expansion) via vaporization of a liquid phase agent (e.g., with minimal thermal energy). In such cases, the vaporization may non-invasively depolarize target neuronal cells. In thermal stimulus, for example, the effect of a gradual transient of thermal energy may be utilized for neural stimulation. As briefly described above, "neuromodulation" may result from the acoustic energy increasing cellular ATP consumption and evoked neuronal depolarization.

FIG. 1D shows an example absorptive element configuration for synergetic photoacoustic/thermal neuromodulation. As shown in FIG. 1D, an absorptive element may be configured as a single absorptive layer, and may be disposed adjacent, or proximate, to a target tissue or region-of-interest of a user (e.g., a user's retinal tissue) in a photoacoustic stimulation and/or thermal stimulation approach. Here, light (e.g., near-infrared laser light) may be directed at, and absorbed by, the absorptive element, which may cause the absorptive element to generate acoustic energy (e.g., highly localized ultrasound waves) that is proportionate to levels of the laser light, and an irradiated volume of the absorptive element to undergo thermoelastic expansion, resulting in depolarization of an underlying retinal ganglion cell layer and increased cellular ATP, thereby providing neural modulation.

FIG. 1E shows another example absorptive element configuration for neuromodulation. As shown in FIG. 1E, an absorptive element may include a piezoelectric component (e.g., BiFeO3 (BFO)-based piezoelectric polymers, which may be lead-free, optically transparent to near-infrared laser light, and/or the like) disposed between two absorptive element layers—e.g., an anterior absorptive layer and a posterior absorptive layer. The configuration may be disposed adjacent, or proximate, to a target tissue or region-of-interest of a user. In some implementations, the piezoelectric component may be partially or fully transparent to light (e.g., such as wavelengths of light ranging from 570 nm to infrared wavelengths and/or the like). In some implementations, the piezoelectric component may include a one-dimensional array of piezoelectric elements. Here, light (e.g., near-infrared laser light) may be directed at the anterior absorptive layer in which a portion of the laser light (e.g., 50% of the laser light) may be absorbed (e.g., in a manner similar to that described above in connection with FIG. 1D), and a remaining portion of the laser light may pass through the transparent piezoelectric component and contact (and be absorbed by) the posterior absorptive layer. This may (e.g., near instantaneously, by virtue of the speed of light) cause acoustic energy to be generated at the anterior absorptive layer and the posterior absorptive layer (e.g., at opposite, or near opposite, directions), which may, in turn, cause the piezoelectric component (e.g., in a localized compression and rarefaction field) to generate an electrical field (e.g., electrical current leakage) that alone, or in combination with the acoustic energies generated by the anterior absorptive layer and the posterior absorptive layer, may provide local stimulation to the neuronal cells. That is, light-based excitation of the absorptive layers may cause volume changes in the absorptive layers, where the limited area, constrained by clamping and/or insulation elements, triggers change(s) in voltage at the piezoelectric component, leading to proportional electrical current change(s) in the target tissue.

In various implementations, other electrical-based absorptive element configuration(s) (e.g., different from that shown in FIG. 1E) may be utilized to provide neural stimulation.

FIG. 1F shows yet another example absorptive element configuration for synergetic photoacoustic/thermal neuromodulation. As shown in FIG. 1F, an absorptive element or layer may be configured as an array in a photoacoustic stimulation and/or thermal stimulation approach. In some implementations, the absorptive element may be composed of a customized photoacoustic-reactive composite. As shown, the absorptive element may include one or more clamping and/or insulation components configured to constrain the absorptive array layer such that the absorptive element exhibits directivity-restricted thermoacoustic expansion (e.g., in an axial direction into a retinal cell area, as shown).

A clamping component may be composed of material(s) having a low thermal expansion coefficient, such as, for example, ceramic material (which may have limited expansibility, serve as a good insulator, and/or prevent acoustic cross-talk) and/or any other type of material configured such that a volume of the material remains constant or substantially constant (e.g., despite being subjected to thermal and/or acoustic energy, such as that generated by an absorptive element).

In some implementations, an absorptive element may include one or more metamaterial structures configured to provide acoustic responses to low-level optical excitations (which may, for example, provide increased focus and spatial resolution for retinal stimulation). A metamaterial structure may be configured such that properties, in one or more dimensions of the metamaterial structures, may be independently controlled. In some implementations, a metamaterial structure may be configured to absorb light so as to maximize photoacoustic pressure generation in a particular direction (e.g., in an axial direction into a retinal cell area). For example, a metamaterial structure may be configured to dissipate heat in one dimension, and not dissipate heat (or dissipate a minimal amount of heat) in one or more other dimensions. This may, for example, enable thermal control where neuronal cells are exposed to a limited amount of heat during use of the photoacoustic-based stimulation system. In some implementations, the metamaterial may be configured to provide anisotropic thermal dissipation, which improves biosafety.

FIG. 1S shows an example absorptive element configuration for neuromodulation based mainly (e.g., only) on mechanical stimulus. As shown in FIG. 1S, an absorptive element (absorptive agent) may be implemented as a liquid, and can change phase and turn into a gas based on an increase in temperature of an environment (e.g., based on temperature reaching a certain threshold). In a case where the temperature returns to a lower temperature (e.g., room temperature and/or the like), the absorptive agent may change phase and turn back into a liquid, enabling repeated use of the absorptive agent. Vaporization of the absorptive agent may be leveraged to provide neuromodulation. In some implementations, light excitation of the absorptive agent may instantaneously (or near-instantaneously) trigger vaporization of the absorptive agent (based on light absorbance by the absorptive agent), resulting in the generation of acoustic energy that can propagate into a target tissue or region-of interest of a user for stimulation. In some implementations, only a limited amount of thermal energy may be needed to trigger the absorptive agent to undergo vaporization. In some implementations, the absorptive agent may include array chambers for containing such vaporization.

Although some implementations are described herein to apply to retinal stimulation, the implementations apply equally or similarly to other types of stimulation, such as motor-based stimulation, auditory stimulation, stimulation for pain management, and/or other stimulation related to a brain and/or nerves. As one example, an absorptive element may be disposed proximate, or adjacent, to a C-fiber that carries pain information for a user, where absorption of light energy (e.g., based on an optimized stimulation sequence) by the absorptive element may cause mechanical neuromodulation (to selectively suppress and/or excite neuronal activity), and thereby suppress the pain information. As another example, an absorptive element may be disposed proximate, or adjacent, to an auditory cortex, or associated nerve(s), of a user, where absorption of light energy (e.g., based on an optimized stimulation sequence) may enable a user to hear. Such an application would be particularly beneficial to alert a user to an emergency situation, for example. As yet another example, an absorptive element may be disposed proximate, or adjacent, to a motor cortex, or muscle-related nerve(s), of a user, where absorption of light energy (e.g., based on an optimized stimulation sequence) may enable the user to move as needed.

FIGS. 1G and 1H are example diagrams of a sample in vitro case of sensory stimulation via photoacoustic effects, including results of the sample case, which verify cell function under such photoacoustic effects. As shown in FIG. 1G, a ytterbium fiber-coupled laser source was used to provide laser energy to a laser head and collimator unit. The laser source was controlled by a computing device (e.g., a workstation) based on control information and/or other data provided by a fluorescence microscopic system. Laser beam(s), outputted by the laser head and collimator unit, were directed at an absorptive element (composed of black rubber) disposed adjacent, or proximate, to neuronal cells in a cell culture. Various stimulation parameters, such as light pulse repetition rate, light pulse energy, light pulse length, exposure duration, were adjusted or optimized to evoke a maximum amount of membrane potential in target neuronal cells.

To detect reactions (e.g., depolarization) of the neuronal cells based on the photoacoustic effects, the neuronal cells were combined (e.g., loaded or mixed) with a voltage sensitive dye configured to emit fluorescence light in response to (e.g., proportionate to) changes in membrane potential due to such depolarization. In the sample case, a fluorescence detector, including a continuous wave light source and camera, was employed to capture images, of the neuronal cells, and to identify levels of the fluorescence light.

As shown in FIG. 1H, in a "sham" case (e.g., where no absorptive element was utilized), no changes in levels of fluorescence, throughout the neuronal cells, was detected in response to photoacoustic-based stimulation. As shown, in cases where the absorptive element was utilized, and laser beam(s) at various frequencies (e.g., 1 kHz for 5 seconds, 2 kHz for 5 seconds, and 2 kHz for 25 seconds) were directed at the absorptive element to generate acoustic (e.g., ultrasound) signals for stimulating the neuronal cells, increased levels of fluorescence were detected, thus verifying cell function under photoacoustic effects.

FIGS. 1I-1L are example diagrams of a sample in vitro case of sensory stimulation via photoacoustic effects, including results of the sample case, which verify cell function under such photoacoustic effects.

As shown in FIG. 1I, a preliminary system configuration included a laser module (including, for example, a laser source capable of producing a laser), an absorptive element composed of polychloroprene (including permeable support structures), fluorescent voltage sensitive dye for tracking neural activation, and an inverted fluorescent microscope for recording changes in fluorescence over time. The laser module is a short-pulse ytterbium fiber laser source having a reinforced armored fiber cable (not shown), capable of emitting radiation at 1060-1080 nanometers (nm), has a maximum power of 31.5 watts, has a pulse repetition rate adjustable from a single pulse to 2 megahertz (MHz), has a pulse width adjustable from 3 nanoseconds (nsec) to 250 nsec, has a line width of 1 nsec to 5 nsec, and has an intrinsic beam diameter of 6 millimeters (mm) to 9 mm.

FIG. 1J shows characterizations of a photoacoustic output signal (obtained based on laser excitation on the absorptive element, and measurements of acoustic energy provided by a hydrophone—not shown) in temporal and frequency domains, where spectral analysis of the photoacoustic output signal ranged from 1 MHz to 20 MHz, at 1 MHz intervals. As shown in FIG. 1J, pulsed laser excitation (11 millijoules (mJ) in total energy at 10 Hertz) generated up to 312 kilopascals (kPa) of mechanical pressure, which corresponds to 4.5 watts per centimeter squared ($cm^2$) in instantaneous peak intensity and 0.226 milliwatts (mW) per $cm^2$ in mean intensity.

Primary cortical neurons (PCNs) were isolated from embryonic day 15 (E15) of gestation, timed-pregnant CD1 mice (where cerebral cortices were dissected, meninges were removed, trypsin was used to obtain a single cell suspension, cells were plated over a poly-1-ornithine coat in neural media containing neurobasal media without glucose, and supplemented with 12.5 millimoles (mM) of glucose, 2% B-27®, and 2 mM of 1-glutamine). PCNs were used between DIV-10 and DIV-14. A voltage sensitive dye (i.e., Bis-(1,3-Dibutylbarbituric Acid)Trimethine Oxonol (DiBAC4(3))) was applied to the PCNs to facilitate tracking of neural activation.

Responses of the PCNs were recorded using fluorescence microscopy. A sham group was used without any photoacoustic-based stimulation, and three different laser pulse widths—100 nsec, 150 nsec, and 200 nsec—were used for photoacoustic-based stimulation groups—i.e., with 0.41 mJ of pulse energy at 5 kHz pulse repetition frequency (2 watts).

As shown in FIG. 1K, fluorescence microscopic images, of sham and photoacoustic-based stimulation groups at pre-stimulation (1 minute) and post-stimulation (6 minute) (where white arrows indicate regions-of-interest for membrane potential quantification), show significant differences between the two groups. The maximal fractional changes of membrane potential of the photoacoustic-based stimulation group and the sham group was 1.45±0.09 and 1.02±0.01, respectively ($P<0.0001$—that is, statistically highly significant). As shown in FIG. 1L, the fractional changes of membrane potential with 100 nsec, 150 nsec, and 200 nsec pulse widths were 1.45±0.09, 1.36±0.04, and 1.15±0.03, respectively, indicating that shorter pulse widths yield greater membrane potential, and thus may be more suitable for photoacoustic-based stimulation of neuronal cells.

FIG. 1M is a diagram of a transmission electron microscopy image of an absorptive element composed of palladium-nanoparticle silicone (PdNS). In a sample case, a PdNS-based absorptive element and polychloroprene-based absorptive element were each subjected to 20 seconds of infrared laser excitation at 0.41-mJ/pulse, and 2.5 kHz repetition rate, to compare thermal dissipation properties. As shown in FIG. 1N, results indicate that the PdNS-based absorptive element exhibited faster heat loss relative to the polychloroprene-based absorptive element (e.g., about twice the rate of heat loss of the polychloroprene-based absorptive element), and thus is a viable material for use as an absorptive element of photoacoustic-based stimulation system implementations described herein.

In some implementations, an in vitro model may be developed (e.g., using primary neurons, such as PCNs, and/or the like) to determine quantitative guidelines or parameters relating to photoacoustic-based stimulation of neuronal cells—e.g., to optimize a mode of laser delivery for photoacoustic-based stimulation, to identify suitable photoacoustic sensitive material(s), to determine photoacoustic-based stimulation parameters, to configure real-time (or near-real time) fluorescent monitoring of neural activity, and/or the like. To detect photoacoustic-based stimulation effects, a negative control group may include cell culture samples that are not subjected to photoacoustic-based stimulation, and yet subjected to the same conditions as cell culture samples that are subjected to photoacoustic-based stimulation. As shown in FIG. 1O, to optimize a mode of laser delivery, a wide laser beam may be utilized in combination with an absorptive element to generate a single large ultrasound wave, or alternatively, in combination with an absorptive element configured to permit generation of multiple (e.g., smaller) ultrasound waves. As shown, a precise steerable laser beam may alternatively be utilized to generate high resolution ultrasound wave patterns.

In some implementations, the in vitro model may enable the identification of suitable materials for the absorptive element, including, for example, PdNS, specialized composite, photoacoustic-reactive materials (e.g., including clamping materials and/or the like), refractory materials (e.g., textured polycrystallines and/or the like), and/or the like. Suitable materials may include those that provide a high (e.g., a maximum) ratio of ultrasound energy output relative to laser energy input (e.g., as measured using a calibrated hydrophone), have high (e.g., superior) heat dissipation properties (e.g., which may help reduce or eliminate the risks of tissue damage), are biocompatible, and/or the like.

In some implementations, the in vitro model may be utilized to determine photoacoustic-based stimulation parameters, such as by analyzing effects of various laser intensity amplitudes, laser pulse widths, laser pulse frequencies, inter-phase intervals, stimulation periods on photoacoustic-mediated neuronal stimulation in PCNs, and/or the like. In some implementations, spatial distribution of an intensity of photoacoustic-based stimulation may be characterized (e.g., via acoustic-based simulations (e.g., using a k-wave simulation tool, via phantom studies, and/or the like)) to determine the spatial resolution of a photoacoustic-based stimulation system when used to provide virtual vision to a user.

In some implementations, fluorescent voltage sensitive dyes (e.g., fast reacting voltage sensitive dyes) may be utilized, in the in vitro model, for real-time (or near real-time) fluorescent monitoring of neural activity. Imaging parameters, such as excitation/emission wavelengths, exposure time, and signal to noise ratio, may be optimized using various dyes and/or probes. In some implementations, calcium sensitive dyes, voltage sensitive fluorescent proteins, and/or the like may be utilized for real-time (or near real-time) monitoring of neural activity.

To prevent, or control, neural network cross talk in a petri dish environment, which may negatively impact the detection of successful pattern stimulations, neurons may be seeded at low densities. In some implementations, fast scanning may be employed to temporally separate the pattern stimulations from subsequent neural network firing.

In a case where photoacoustic-induced heat generation satisfies (e.g., exceeds) one or more thresholds, temporal laser patterning may be employed to dampen the heat generation at one or more points of the absorptive element. In some implementations, a distance between the absorptive element and target neurons may be varied to mimic epi-corneal, epi-retinal, sub-retinal, and/or supra-choroidal placement of the absorptive element.

In some implementations, an early stage human eye-like model may be developed and used for determining various photoacoustic-based stimulation guidelines or parameters. In some implementations, PCNs may be cultured on coverslips, and inserted into a human eye-like model to simulate a retina so as to determine a feasibility of epi-corneal photoacoustic-based stimulation of neurons, to determine an optical location to mount an absorptive element relative to the retina, to identify heat generation/dissipation properties of photoacoustic neuromodulation (e.g., a rate of heat generation in the absorptive element, a rate of heat dissipation in the eye, and/or the like), and/or the like.

Various physical parameters may be considered and factored into the design, or configuration, of materials for use as the absorptive element, including (e.g., as described above) thermal dissipation properties—e.g., a ratio of a thermal stress coefficient to a heat capacity of a material (e.g., the Grüneisen parameter). As some examples, a suitable material, for use as the absorptive element, may include a homogeneous, isotropic material or a composite material. For proper operation in an environment of the near-retinal region in an eye, the material may be acoustically-matched to maximize sound transmission into the retina, may have high optical absorption to prevent optical transmission into the retina, may have high thermal diffusivity to prevent damage to the material as well as surrounding tissue, and/or the like. In some cases, the material may have a large thermal effusivity mismatch with a retina, which may confine thermal energy to the material, and thus prevent thermal damage to the surrounding tissue. Some implementations may include confining optical absorbers (and thus and photothermal conversion) to one side (e.g., a vitreous side) of the material to provide thermal relief to the retina.

In some cases, anisotropic thermal diffusion/expansion may be employed to further dissipate heat from an excitation region and from the retina. Anisotropic thermal diffusion/expansion may additionally increase forward-directed acoustic transmissions, while reducing lateral expansion that might produce unwanted shearing stresses at the material-retina boundary. In some implementations, graded-interface technique(s) may be employed for acoustic impedance matching (e.g., to increase acoustic energy transmissions toward the retina, while reducing such acoustic energy transmissions into the vitreous).

Various techniques (e.g., such as those used for developing polymer matrix nanocomposites (PMNCs)) may be utilized to fabricate suitable composite materials (e.g., PMNC-based materials) for use as the absorptive element. In some implementations, a composite material may be produced with a variety of nanoparticulate reinforcements that serve as photothermal converters, where the distribution of such nanoparticulate reinforcements may be controlled to obtain desired heating in the composite material. Polymer matrices may also be defined to provide a PMNC-based material having desired optical and/or thermal properties— e.g., to achieve desired acoustic impedance characteristics, desired biocompatibility, desired anisotropic thermal expansion, and/or the like.

In some implementations, the human eye-like model may be produced via a gel material (e.g., containing an internal vitreous-like fluid) and a PCN layer (e.g., to simulate a retina). In some implementations, a circulation system (e.g., a mini-fluid circulation system) may be included to simulate a vascular network beneath a retina. In some implementations, the material may be disposed internally, and adjacent to, the PCN layer so as to emulate the photoacoustic-based stimulation system implementations described above in connection with FIGS. 1A and/or 1C. In some implementations, the material may be disposed externally from the PCN layer so as to emulate the non-invasive photoacoustic-based stimulation system implementation described above in connection with FIG. 1B.

In some implementations, systematic temperature measurements may be taken (e.g., subsequent to repeated photoacoustic-based stimulation) at a surface of the material, at the PCN layer, in the circulating fluid, and/or at the vitreous-like fluid. In some implementations, resulting neuronal stimulation may be detected via fluorescence of voltage sensitive dyes, as described above in connection with FIGS. 1G-1L.

In some implementations, various photoacoustic-based stimulation systems may be developed and provided for modeling photoacoustic neuromodulation—e.g., to verify photoacoustic-based retinal neuromodulation by measuring activation of the visual cortex, to verify perception of retinal neuromodulation as vision, or virtual vision, based on behavioral responses, and/or the like. FIGS. 1P and 1Q are diagrams of example photoacoustic-based stimulation systems configured to provide bi-ocular spotted stimulation (e.g., based on customized stimulation sequences) for an animal, such as a rodent. In some implementations, such systems may be sufficiently compact to facilitate installation near, on, or within an eye cavity of a visually-impaired rodent (e.g., a diameter of about 3 to 4 millimeters). In some implementations, system components may be positioned (e.g., affixed) so as to provide retinal stimulation (e.g., based on photoacoustic-based stimulation parameters or guidelines described above) via photoacoustic pressure generated by an absorptive element coupled to a retinal layer of a rodent. In some implementations, portions of a coupling gel, within an eye cavity, may be dissipated prior to installing the absorptive element.

As shown in FIGS. 1P and 1Q, a photoacoustic-based stimulation system may be configured as a wearable apparatus—e.g., a helmet—configured to be positioned on and coupled to a head of a rodent. In some implementations, an inner surface of the helmet may be overlaid with rubberized material so as to provide a general fit to rodents having different anatomical head morphologies. In some implementations, an optical imager (e.g., a motorized mirror system) may be integrated in a pulsed laser source to induce retinal stimulation on the rodent's ocular system (e.g., in a side-by-side manner), where a single laser source may stimulate both eyes without compromising any of the photoacoustic-based stimulation parameters or guidelines. In some implementations, responses to photoacoustic-based stimulation may be validated using electroencephalogram (EEG) measurements. In some cases, thermal dissipation on a surface of the absorptive element disposed adjacent, or proximate, to the retinal layer may be measured (e.g., via a thermal camera and/or the like) and controlled in preparation for in vivo applications.

In some cases, rodent(s) may be trained to respond to light or patterns with specified behavioral responses, after which light may be replaced with photoacoustic neuromodulation to confirm that the perception of retinal stimulation provides vision or virtual vision. In some implementations, an optical fiber bundle may be utilized, in combination with the photoacoustic-based helmet, to deliver photoacoustic-based stimulation to a rodent's eye to provide non-invasive retinal neuromodulation.

In some implementations, calibrations may be made to maximize electrophysiological signals in EEG measurements. In some implementations, an acoustically-transparent insulation material may be included between the absorptive element and the retinal layer to improve thermal biosafety. In some implementations, and as described elsewhere herein, the absorptive element may include a metamaterial structure for improved thermal biosafety (e.g., via anisotropic thermal dissipation to prevent heat conduction on the retinal layer).

In some implementations, a visual cortex monitoring system may be provided to monitor photoacoustic-based stimulation effects (e.g., in real-time or near real-time), and quantitatively validate appropriate levels of stimulation that may be provided to the visual cortex via the optic nerve pathway. In some implementations, the visual cortex monitoring system may be configured to provide feedback to a photoacoustic-based stimulation system. Monitoring visual cortex activities may permit calibration of a location and/or an orientation (e.g., an angle) of the photoacoustic-based stimulation system for installation purposes, and determination of optimized photoacoustic-based stimulation parameters, while taking into consideration anatomic variances among users and maximization of user safety. For example, monitoring visual cortex activities, when the photoacoustic-based stimulation system is employed during a user's typical everyday activities, may permit determination of a minimal pulse energy for a given patient.

FIG. 1R shows a visual cortex monitoring system integrated, or in communication, with a photoacoustic-based stimulation system (e.g., the photoacoustic-based stimulation system implementation described above in connection with FIG. 1C). Although not shown, the visual cortex monitoring system may alternatively be integrated, or be in communication, with another photoacoustic-based stimulation system implementation, such as one of the photoacoustic-based stimulation system implementations described above in connection with FIGS. 1A and 1B.

As shown in FIG. 1R, the visual cortex monitoring system may include a processor, a data acquisition device, a photoacoustic probe, and an optical parametric oscillator (e.g., a neodymium-doped yttrium aluminum garnet (Nd:YAG) laser source and/or the like). In some implementations, the photoacoustic-based stimulation system may include a power source (e.g., one or more batteries) that provides power for the various components of the visual cortex monitoring system.

As further shown in FIG. 1R, the photoacoustic probe may monitor brain activity in a visual cortex region of a brain (e.g., based on photoacoustic-based stimulation provided by the photoacoustic-based stimulation system), and provide corresponding signals to the data acquisition device. In some implementations, a voltage sensitive dye may be injected into a user, and an adenosine receptor (e.g., regadenoson) may be utilized to open a blood brain barrier to enable the voltage sensitive dye to reach the visual cortex region, and thus permit the photoacoustic probe to detect brain activity. The processor, of the visual cortex monitoring system, may process the signals to determine stimulation effects, and provide, to the photoacoustic-based stimulation system (e.g., to the processor(s) of the photoacoustic-based stimulation system), information regarding the stimulation effects—e.g., calibration data—which the photoacoustic-based stimulation system may utilize to calibrate photoacoustic-based stimulation parameters.

In this way, the visual cortex monitoring system may provide closed-loop feedback to the photoacoustic-based stimulation system, which enables adaptable stimulation for users with different ocular anatomies, maximizes the performance of the photoacoustic-based stimulation system, and improves overall user safety.

In sample cases, visual cortex analysis was performed (e.g., in a global epileptic seizure model), for example, to validate efficacy of such monitoring. See, for example, Jeeun Kang et al., "Transcranial photoacoustic imaging of NMDA-evoked focal circuit dynamics in rat forebrain," https://www.biorxiv.org/content/early/2018/04/13/202408, bioRxiv, Apr. 13, 2018 and Jeeun Kang et al., "Transcranial photoacoustic imaging of NMDA-evoked focal circuit dynamics in rat forebrain," https://www.biorxiv.org/content/early/2018/05/05/308585.1, bioRxiv, May 5, 2018, which are both incorporated by reference herein in their entireties.

In some implementations, in vivo validation of photoacoustic neuromodulation and visual cortex monitoring and/or recording (e.g., such as that described above in connection with FIG. 1R) may involve subjecting each eye of an animal—e.g., a rodent—to various temporal patterns to determine corresponding responses (e.g., visual cortex monitoring readouts) on the rodent's visual cortex. In cases where significant visual activity is not detected in the visual cortex, a wider range of photoacoustic-based stimulation parameters may be utilized to address any anatomical variations, interferential artifacts between the photoacoustic-based stimulation system and the visual cortex monitoring system, and/or the like.

In this way, the system(s) enable enhanced stimulation resolution and deeper penetration of neuronal cells, thus providing more effective virtual sensory functionality for users. For example, excitation of an absorptive element and/or the like (e.g., to cause thermal stimulation and/or vaporization-based stimulation of neuronal cells) can result in depolarization of neuronal cells in controlled spatiotemporal resolution, providing sensory perception to a user such that the user may visually and/or auditorily perceive an environment, be alleviated from pain (e.g., from disease and/or the like) (e.g., via inhibition(s) to C-fiber nerves), become manipulated to perform motor function(s) (e.g., via muscle nerve and/or motor cortex stimulation), and/or the like. In cases where system implementations described herein are applied to a user's retinal neurons, for example, the user can experience improved virtual vision—e.g., fast and fine resolution of vision, such as that at greater than 64 static pixels of information. In addition, non-invasive, and compact, system implementations described herein reduce or eliminate a need for patients to undergo sensory-related implant surgeries (e.g., to a retina and/or the like), thereby reducing treatment costs and improving user safety. Furthermore, the use of a laser-based photoacoustic-based stimulation system (that leverages laser light) permits fine control of light pulse durations and targeting of light energy, which provides a high degree of operative flexibility. Moreover, closed-loop feedback, provided by the visual cortex monitoring system, also enables adaptive stimulation (e.g., for users with different ocular anatomies), which maximizes the performance of the photoacoustic-based stimulation system, and improves user safety.

As indicated above, FIGS. 1A-1S are provided merely as examples. Other examples are possible and may differ from what was described with regard to FIGS. 1A-1S.

Figure 2:
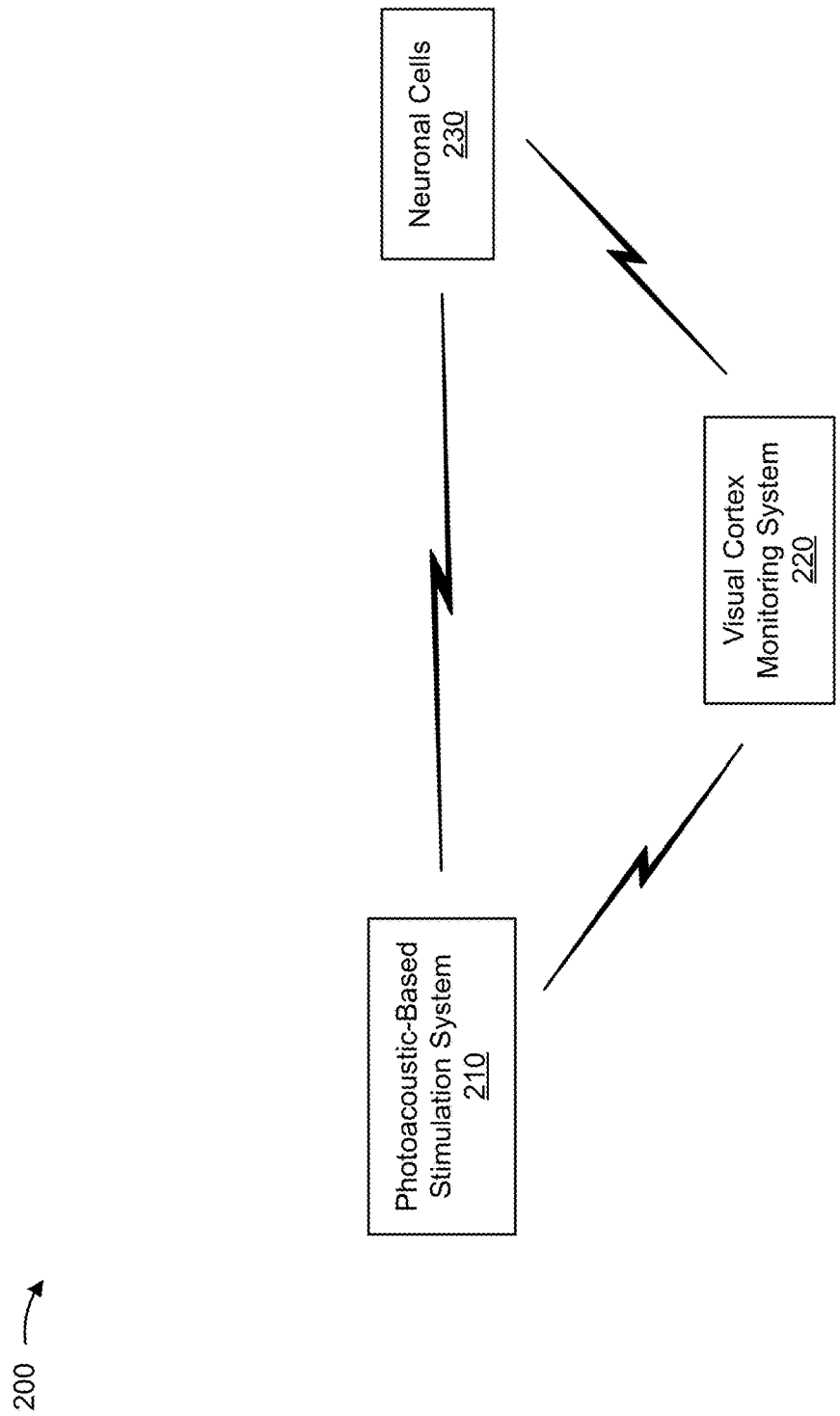
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include a photoacoustic-based stimulation system 210, a visual cortex monitoring system 220, and neuronal cells 230.

Photoacoustic-based stimulation system 210 includes one or more systems, devices, and/or components configured to capture images of an environment, process the images, generate light based on processing the images, and/or directing the generated light onto one or more absorptive elements, as described elsewhere herein. For example, photoacoustic-based stimulation system 210 may include one or more image capturing components, one or more processors, one or more light projection devices, and/or one or more power sources (e.g., one or more batteries) that provide power for the various components of photoacoustic-based stimulation system 210.

The image capturing component(s) may include one or more cameras or one or more electronic devices that incorporate camera(s) for capturing images or video. In some implementations, the image capturing component(s) may be configured to capture images or video of an environment of a user, as described elsewhere herein. The processor(s) may include one or more types of processing components capable of being programmed to perform a function, such as one or more operations described elsewhere herein. For example, the processor(s) may perform process 400 of FIG. 4, process 500 of FIG. 5, process 600 of FIG. 6, and/or the like. In some implementations, the processor(s) may be configured to process images captured by the image capturing component(s), such as by performing intensity truncation, coordination conversion, and providing captured images to the light projection device(s) in real-time, as described elsewhere herein. In some implementations, the processor(s) may correspond to a processor, described in more detail below in connection with FIG. 3.

The light projection device may include a controller (e.g., a real-time controller and/or the like) communicatively coupled to the processor(s), a light source (e.g., one or more laser sources (e.g., laser projector(s), such as pico-projector(s)) and/or the like) communicatively coupled to the controller, and an optical imager or scanner. The controller may include one or more types of processing components capable of being programmed to perform a function, such as one or more operations described elsewhere herein. For example, the controller may perform process 400 of FIG. 4, process 500 of FIG. 5, process 600 of FIG. 6, and/or the like. In some implementations, the controller may correspond to a processor, described in more detail below in connection with FIG. 3. The light source may include a laser source based one or more elements, such as erbium, ytterbium, neodymium, dysprosium, praseodymium, thulium, holmium, and/or the like. In some implementations, the light source may provide pulsed (e.g., non-injurious) light energy based on commands provided by the controller, as described elsewhere herein.

The optical imager may include one or more mirrors (e.g., a dual-axis scanner) configured to permit raster scanning, and directing, of light from the light source, to one or more materials. For example, the optical imager may include one or more miniaturized galvo-mirrors, MEMS actuators, and/ or the like. In some implementations, the optical imager may, under control of the processor(s) and/or the controller, raster scan laser beam(s) onto an absorptive element, as described elsewhere herein.

In some implementations, photoacoustic-based stimulation system 210 may include an absorptive element or component. The absorptive element may include one or more biocompatible materials configured to absorb light energy (e.g., near-infrared laser energy and/or the like) and generate acoustic signals (e.g., ultrasound signals or beams and/or the like) based on the light energy. In some implementations, the absorptive element may exhibit high light absorbance characteristics and high thermal durability, as described elsewhere herein. For example, the absorptive element may be composed of polychloroprene, PMNCs, PdNS, a refractory material (e.g., textured polycrystallines and/or the like), polydimethylsiloxane (PDMS) films (e.g., a mixture of PDMS and carbon black and/or the like), and/or another photoacoustic-reactive material. In some implementations, the absorptive element may be positioned proximate to, adjacent to, or over a patient's or user's body part (e.g., the user's eye), or surgically coupled to the user's tissue, to stimulate associated neuronal cells (e.g., neuronal cells 230), as described elsewhere herein.

Visual cortex monitoring system 220 includes one or more systems, devices, and/or components configured to monitor and/or record photoacoustic-based stimulation effects on neuronal cells, such as neuronal cells 230. In some implementations, visual cortex monitoring system 220 may be configured to communicate with a photoacoustic-based stimulation system (e.g., photoacoustic-based stimulation system 210). Visual cortex monitoring system 220 may include one or more processors, one or more data acquisition devices, one or more photoacoustic probes, and/or one or more optical parametric oscillators.

The photoacoustic probe(s) may include one or more devices (e.g., EEG-based devices) capable of monitoring brain activity (e.g., based on photoacoustic-based stimulation provided by photoacoustic-based stimulation system 210) in a visual cortex region of a brain, and provide corresponding signals to the data acquisition device. The processor(s) may include one or more types of processing components capable of being programmed to perform a function, such as one or more operations described elsewhere herein. For example, the processor(s) may perform process 400 of FIG. 4, process 500 of FIG. 5, process 600 of FIG. 6, and/or the like. In some implementations, the processor(s) may correspond to a processor, described in more detail below in connection with FIG. 3. In some implementations, the processor(s) may process the signals, provided by the photoacoustic probe(s), to determine stimulation effects, and provide, to photoacoustic-based stimulation system 210 (e.g., to the processor(s) of photoacoustic-based stimulation system 210), information regarding the stimulation effects for purposes of calibrating photoacoustic-based stimulation parameters, as described elsewhere herein.

Neuronal cells 230 include one or more types of cells associated with a sensory system of a nervous system of a patient or user (e.g., a person, a rodent, or another type of animal or living being). For example, neuronal cells 230 may include cells associated with vision (e.g., retinal cells), cells associated with hearing, cells associated with smell, and/or the like. As another example, neuronal cells 230 may include cells located in or within a patient's or user's brain, such as a visual cortex region of the brain. In some implementations, neuronal cells 230 may be stimulated based on photoacoustic effects to enable a user or patient to perceive an environment, as described elsewhere herein.

The number and arrangement of systems and/or components shown in FIG. 2 are provided as an example. In practice, there may be additional systems and/or components, fewer systems and/or components, different systems and/or components, or differently arranged systems and/or components than those shown in FIG. 2. Furthermore, two or more systems and/or components in FIG. 2 may be implemented within a single system and/or component, or a single system and/or component shown in FIG. 2 may be implemented as multiple, distributed systems and/or components. Additionally, or alternatively, a set of systems and/or components (e.g., one or more system and/or one or more components) of environment 200 may perform one or more functions described as being performed by another set of systems and/or components of environment 200.

Figure 3:
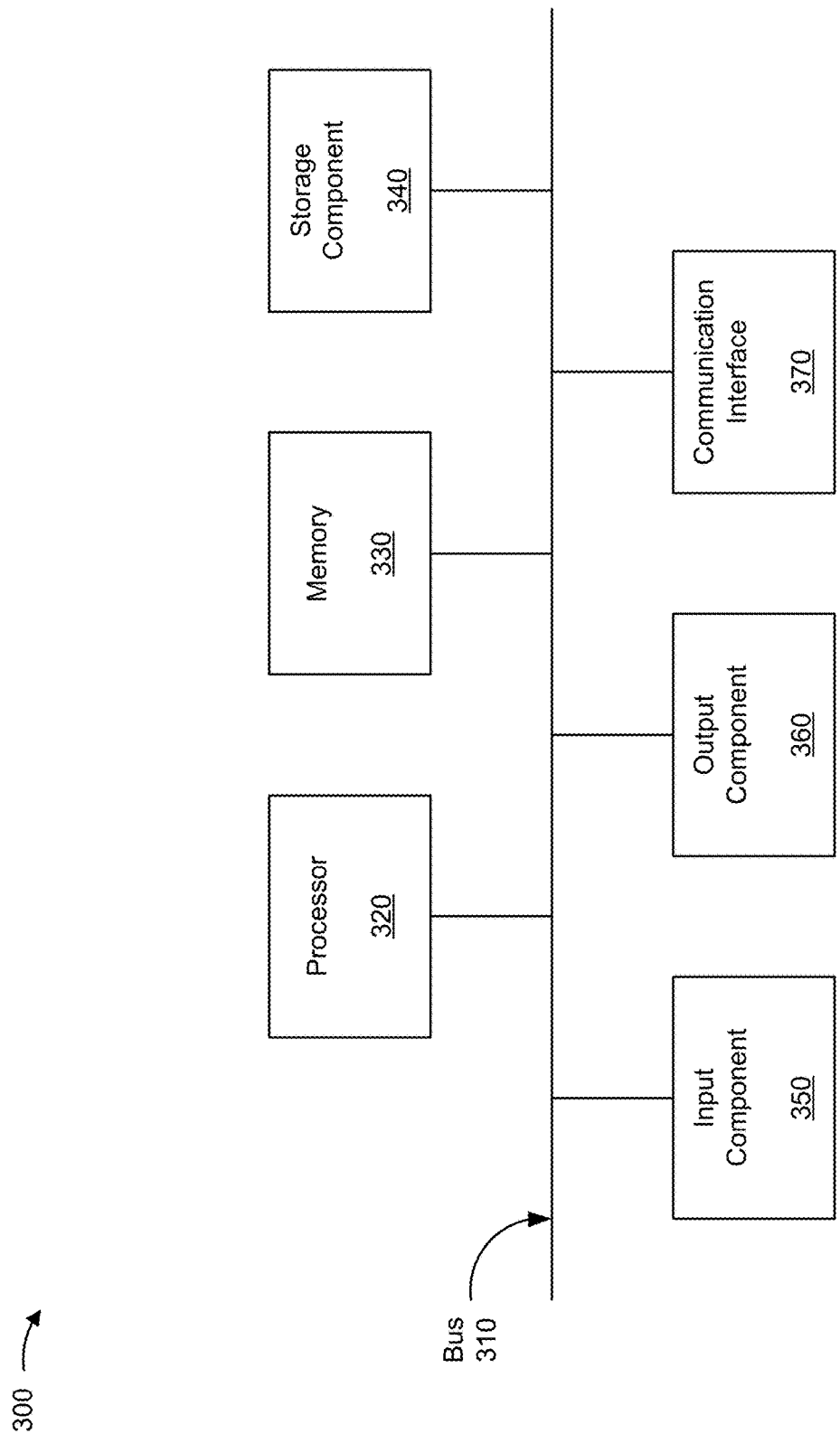
FIG. 3 is a diagram of example components of one or more devices of FIG. 2.

FIG. 3 is a diagram of example components of a device 300. Device 300 may correspond to photoacoustic-based stimulation system 210 and/or visual cortex monitoring system 220. In some implementations, photoacoustic-based stimulation system 210 and/or visual cortex monitoring system 220 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more LEDs).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a wireless local area network interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

Figure 4:
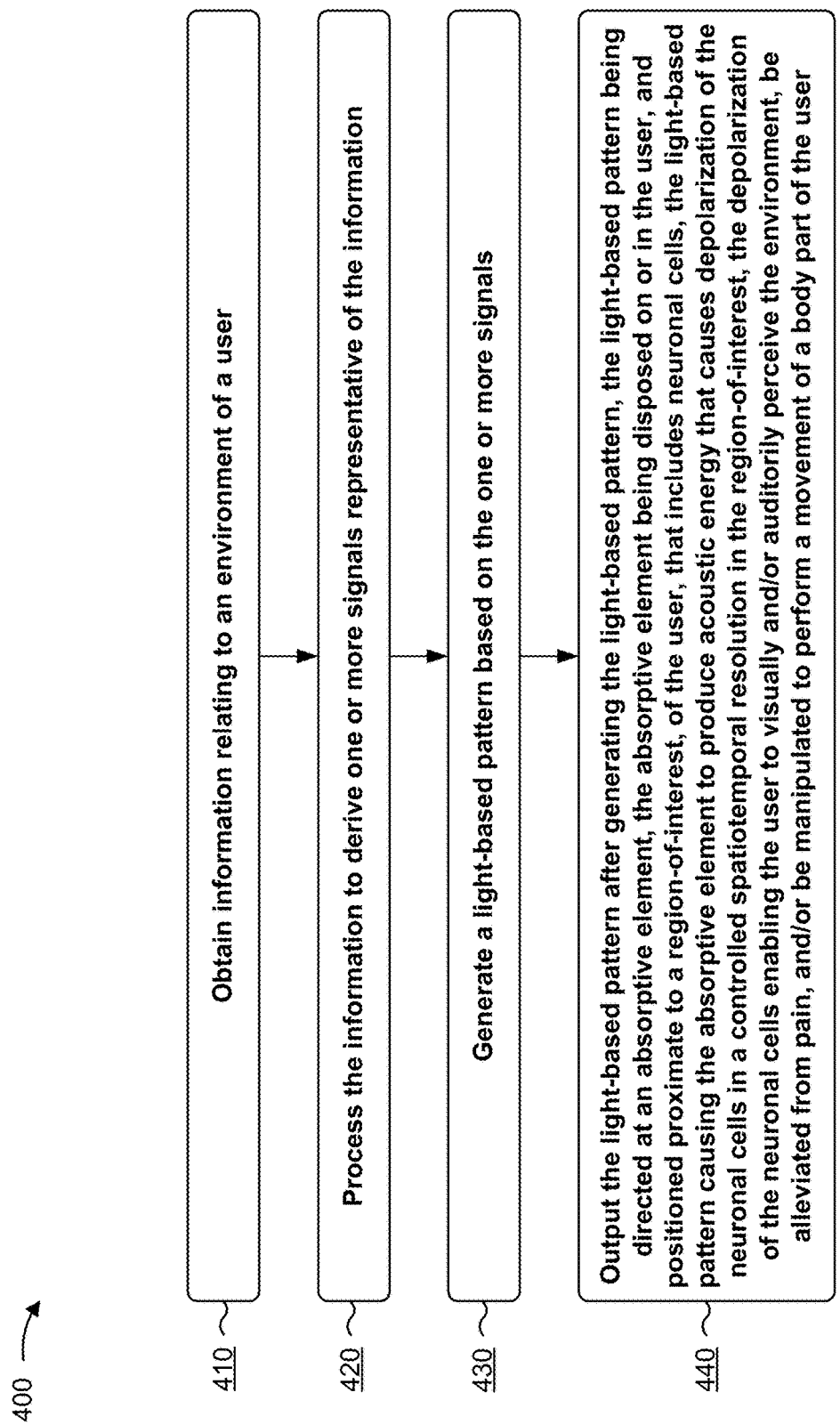
FIG. 4 is a flow chart of an example process for providing neuronal cell stimulation using photoacoustic effects.

FIG. 4 is a flow chart of an example process 400 for providing neuronal cell stimulation using photoacoustic effects. In some implementations, one or more process blocks of FIG. 4 may be performed by a photoacoustic-based stimulation system (e.g., photoacoustic-based stimulation system 210). In some implementations, one or more process blocks of FIG. 4 may be performed by another device or a group of devices separate from or including the photoacoustic-based stimulation system, such as a visual cortex monitoring system (e.g., visual cortex monitoring system 220).

As shown in FIG. 4, process 400 may include obtaining information relating to an environment of a user (block 410). For example, the photoacoustic-based stimulation system (e.g., using processor 320, memory 330, storage component 340, input component 350, communication interface 370, and/or the like) may obtain information relating to an environment of a user, as described above in connection with FIGS. 1A-1S.

As further shown in FIG. 4, process 400 may include processing the information to derive one or more signals representative of the information (block 420). For example, the photoacoustic-based stimulation system (e.g., using processor 320, memory 330, storage component 340, and/or the like) may process the information to derive one or more signals representative of the information, as described above in connection with FIGS. 1A-1S.

As further shown in FIG. 4, process 400 may include generating a light-based pattern based on the one or more signals (block 430). For example, the photoacoustic-based stimulation system (e.g., using processor 320, memory 330, storage component 340, and/or the like) may generate a light-based pattern based on the one or more signals, as described above in connection with FIGS. 1A-1S.

As further shown in FIG. 4, process 400 may include outputting the light-based pattern after generating the light-based pattern (block 440). For example, the photoacoustic-based stimulation system (e.g., using processor 320, memory 330, storage component 340, output component 360, communication interface 370, and/or the like) may output the light-based pattern after generating the light-based pattern, as described above in connection with FIGS. 1A-1S. In some implementations, the light-based pattern may be directed at an absorptive element. In some implementations, the absorptive element may be disposed on or in the user, and positioned proximate to a region-of-interest, of the user, that includes neuronal cells. In some implementations, the light-based pattern may cause the absorptive element to produce acoustic energy that causes depolarization of the neuronal cells in a controlled spatiotemporal resolution in the region-of-interest. In some implementations, the depolarization of the neuronal cells may enable the user to visually and/or auditorily perceive the environment, be alleviated from pain, and/or be manipulated to perform a movement of a body part of the user.

Process 400 may include additional implementations, such as any single implementation or any combination of implementations described below and/or in connection with one or more other processes described elsewhere herein.

In some implementations, the information may include image information. In some implementations, the region-of-interest may include retinal tissue. In some implementations, the information may include image information. In some implementations, the region-of-interest may include tissue of a visual cortex region of a brain of the user.

In some implementations, the information may include audio information. In some implementations, the region-of-interest may include tissue relating to hearing function. In some implementations, the acoustic energy may include ultrasound energy. In some implementations, the light-based pattern may include a laser beam pattern.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

Figure 5:
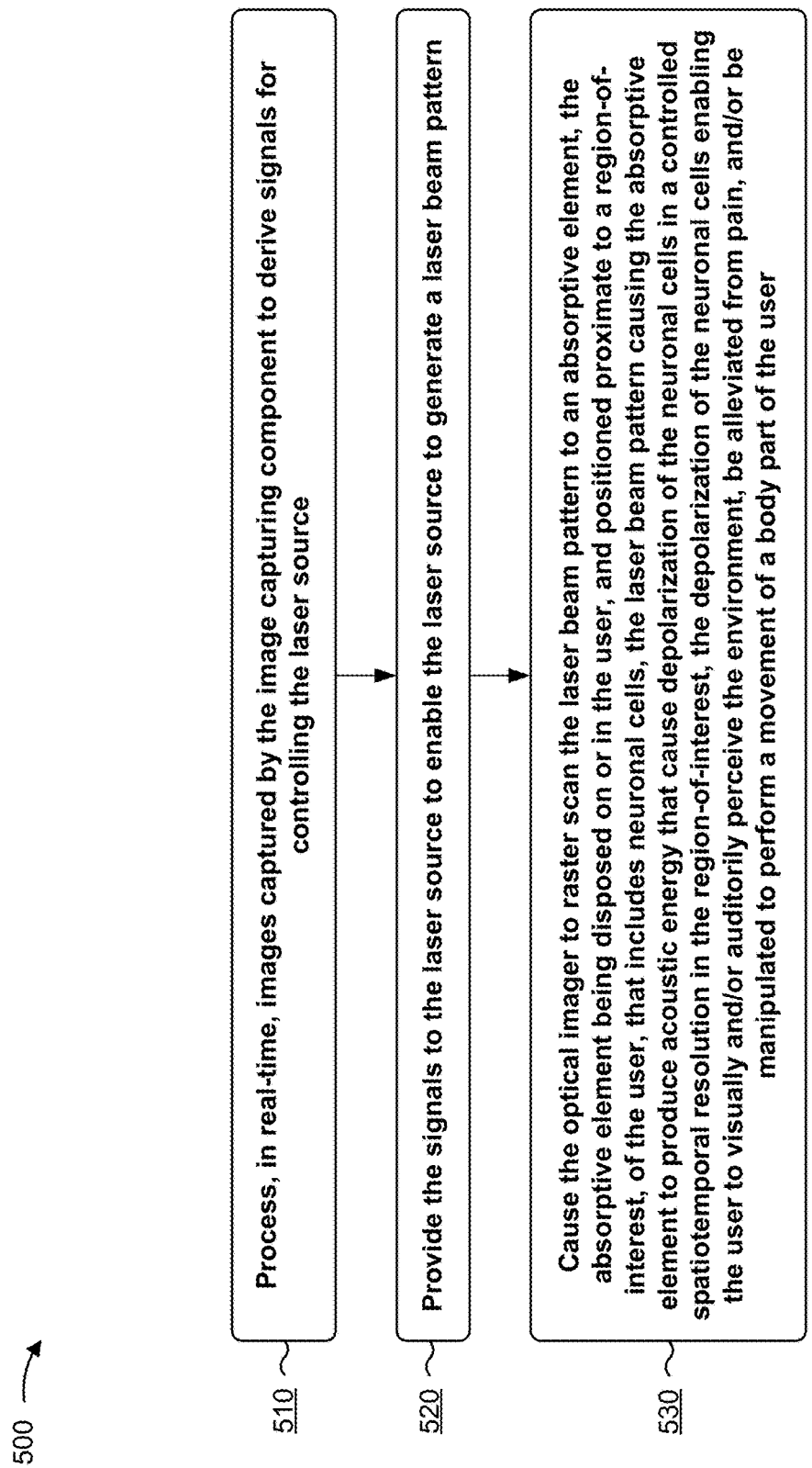
FIG. 5 is a flow chart of an example process for providing neuronal cell stimulation using photoacoustic effects.

FIG. 5 is a flow chart of an example process 500 for providing neuronal cell stimulation using photoacoustic effects. In some implementations, one or more process blocks of FIG. 5 may be performed by a photoacoustic-based stimulation system (e.g., photoacoustic-based stimulation system 210). In some implementations, one or more process blocks of FIG. 5 may be performed by another device or a group of devices separate from or including the photoacoustic-based stimulation system, such as a visual cortex monitoring system (e.g., visual cortex monitoring system 220). In some implementations, a device (e.g., the photoacoustic-based stimulation system) may include an image capturing component to obtain images of an environment of a user, and a light projection system. In some implementations, the light projection system may include a laser source and an optical imager. In some implementations, the device may include one or more memories, and one or more processors, communicatively coupled to the one or more memories, to perform process 500.

As shown in FIG. 5, process 500 may include processing, in real-time, images captured by the image capturing component to derive signals for controlling the laser source (block 510). For example, the photoacoustic-based stimulation system (e.g., using processor 320, memory 330, storage component 340, and/or the like) may process, in real-time, images captured by the image capturing component to derive signals for controlling the laser source, as described above in connection with FIGS. 1A-1S.

As further shown in FIG. 5, process 500 may include providing the signals to the laser source to enable the laser source to generate a laser beam pattern (block 520). For example, the photoacoustic-based stimulation system (e.g., using processor 320, memory 330, storage component 340, output component 360, communication interface 370, and/or the like) may provide the signals to the laser source to enable the laser source to generate a laser beam pattern, as described above in connection with FIGS. 1A-1S.

As further shown in FIG. 5, process 500 may include causing the optical imager to raster scan the laser beam pattern to an absorptive element (block 530). For example, the photoacoustic-based stimulation system (e.g., using processor 320, memory 330, storage component 340, and/or the like) may cause the optical imager to raster scan the laser beam pattern to an absorptive element, as described above in connection with FIGS. 1A-1S. In some implementations, the absorptive element may be disposed on or in the user, and positioned proximate to a region-of-interest, of the user, that includes neuronal cells. In some implementations, the laser beam pattern may cause the absorptive element to produce acoustic energy that causes depolarization of the neuronal cells in a controlled spatiotemporal resolution in the region-of-interest. In some implementations, the depolarization of the neuronal cells may enable the user to visually and/or auditorily perceive the environment, be alleviated from pain, and/or be manipulated to perform a movement of a body part of the user.

Process 500 may include additional implementations, such as any single implementation or any combination of implementations described below and/or in connection with one or more other processes described elsewhere herein.

In some implementations, the laser source and/or the optical imager may be implanted within a cavity of an eye of the user. In some implementations, the region-of-interest may include retinal tissue. In some implementations, the optical imager may include a pair of galvanic mirrors and one or more microelectromechanical system (MEMS) actuators.

In some implementations, the device may be disposed entirely exterior to the user. In some implementations, the device may be implemented in a glasses frame. In some implementations, the laser beam pattern may cause the absorptive element to produce the acoustic energy via thermoelastic expansion of the absorptive element.

In some implementations, the absorptive element may be composed of biocompatible material. In some implementations, the absorptive element may include a metamaterial structure. In some implementations, a physical property of the metamaterial structure may be defined so as to prevent thermal damage to the neuronal cells.

In some implementations, the absorptive element may include an anterior absorptive layer, a posterior absorptive layer, and a diced piezoelectric array disposed between the anterior absorptive layer and the posterior absorptive layer. In some implementations, the diced piezoelectric array may be substantially transparent to light, and capable of generating an electric field, for stimulating the neuronal cells, based on acoustic energy provided by the anterior absorptive layer and the posterior absorptive layer.

Although FIG. 5 shows example blocks of process 500, in some implementations, process 500 may include additional blocks, fewer blocks, different blocks, or differently arranged blocks than those depicted in FIG. 5. Additionally, or alternatively, two or more of the blocks of process 500 may be performed in parallel.

Figure 6:
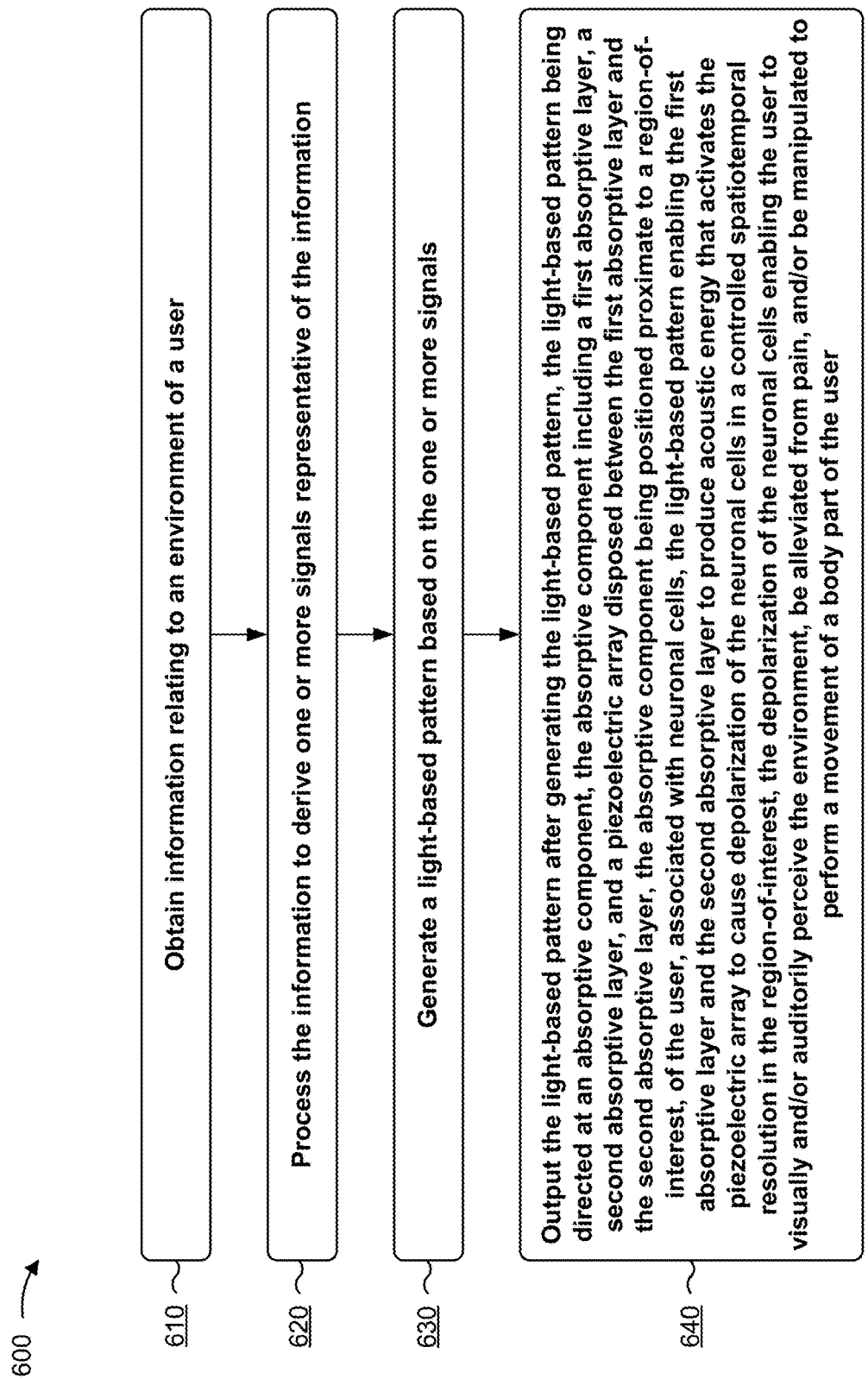
FIG. 6 is a flow chart of an example process for providing neuronal cell stimulation using photoacoustic effects.

FIG. 6 is a flow chart of an example process 600 for providing neuronal cell stimulation using photoacoustic effects. In some implementations, one or more process blocks of FIG. 6 may be performed by a photoacoustic-based stimulation system (e.g., photoacoustic-based stimulation system 210). In some implementations, one or more process blocks of FIG. 6 may be performed by another device or a group of devices separate from or including photoacoustic-based stimulation system 210, such as a visual cortex monitoring system (e.g., visual cortex monitoring system 220). In some implementations, a non-transitory computer-readable medium may store instructions. In some implementations, the instructions may include one or more instructions that, when executed by one or more processors, cause the one or more processors to perform process 600.

As shown in FIG. 6, process 600 may include obtaining information relating to an environment of a user (block 610). For example, the photoacoustic-based stimulation system (e.g., using processor 320, memory 330, storage component 340, input component 350, communication interface 370, and/or the like) may obtain information relating to an environment of a user, as described above in connection with FIGS. 1A-1S.

As further shown in FIG. 6, process 600 may include processing the information to derive one or more signals representative of the information (block 620). For example, the photoacoustic-based stimulation system (e.g., using processor 320, memory 330, storage component 340, and/or the like) may process the information to derive one or more signals representative of the information, as described above in connection with FIGS. 1A-1S.

As further shown in FIG. 6, process 600 may include generating a light-based pattern based on the one or more signals (block 630). For example, the photoacoustic-based stimulation system (e.g., using processor 320, memory 330, storage component 340, and/or the like) may generate a light-based pattern based on the one or more signals, as described above in connection with FIGS. 1A-1S.

As further shown in FIG. 6, process 600 may include outputting the light-based pattern after generating the light-based pattern (block 640). For example, the photoacoustic-based stimulation system (e.g., using processor 320, memory 330, storage component 340, output component 360, communication interface 370, and/or the like) may output the light-based pattern after generating the light-based pattern, as described above in connection with FIGS. 1A-1S. In some implementations, the light-based pattern may be directed at an absorptive component. In some implementations, the absorptive component may include a first absorptive layer, a second absorptive layer, and a piezoelectric array disposed between the first absorptive layer and the second absorptive layer. In some implementations, the absorptive component may be positioned proximate to a region-of-interest, of the user, associated with neuronal cells. In some implementations, the light-based pattern may enable the first absorptive layer and the second absorptive layer to produce acoustic energy that causes depolarization of the neuronal cells in a controlled spatiotemporal resolution in the region-of-interest. In some implementations, the depolarization of the neuronal cells may enable the user to visually and/or auditorily perceive the environment, be alleviated from pain, and/or be manipulated to perform a movement of a body part of the user.

Process 600 may include additional implementations, such as any single implementation or any combination of implementations described below and/or in connection with one or more other processes described elsewhere herein.

In some implementations, the one or more instructions, when executed by the one or more processors, may further cause the one or more processors to receive calibration data from the visual cortex monitoring system, and adjust the light-based pattern based on the calibration data.

In some implementations, the absorptive component may include a clamping material that limits thermal expansion of the absorptive component to one axis of the absorptive component.

In some implementations, the absorptive component may be composed of palladium-nanoparticle silicone (PdNS).

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Some implementations, described herein, provide a photoacoustic-based stimulation system 210 that is capable of stimulating neurons (or neuronal cells) using photoacoustic effects. In some implementations, photoacoustic-based stimulation system 210 is capable of directing light (e.g., a near-infrared laser light) at a photoacoustic sensitive element or absorptive element or layer, disposed proximate to the neuronal cells, to generate highly localized acoustic energy (e.g., ultrasound waves). The acoustic energy causes an increase in cellular ATP consumption and induces depolarization of the neuronal cells (via thermal expansion of the absorptive element (e.g., gradual transient of thermal energy)), resulting in neural modulation. In some implementations, photoacoustic-based stimulation system 210 includes an image capturing component (e.g., including one or more cameras) configured to capture images, one or more processors configured to process the captured images, and an external or intra-cavity light projection system that includes a near-infrared laser source, a processor (e.g., a real-time, or near real-time, controller) configured to cause the near-infrared laser source to output laser light pulses based on the processed images, and an optical imager configured to direct the light pulses at the absorptive element to generate acoustic energy. Photoacoustic-based stimulation system 210 is capable of being adapted for use with any type of neuronal cell relating to brain function, such as, for example, neuronal cells associated with vision or hearing. Thus, in any case, a biocompatible, light absorptive element may be disposed proximate, or adjacent, to a region-of-interest (e.g., tissue and/or the like) for stimulation, and excited with light energy (e.g., at appropriate wavelength(s)) (e.g., selected by considering light penetration and mechanical energy and/or thermal energy needed for appropriate stimulation)) so as to cause mechanical energy and/or thermal energy to be generated. In a case where photoacoustic-based stimulation system 210 is adapted for use with a user's retinal cells, the photoacoustic-based stimulation system is capable of providing virtual vision to the user (e.g., where, even in situations where light perceiving cones and rods may be damaged, light transduction on the user's ocular system causes bipolar cells and ganglion cells to become depolarized, thus permitting visual information to be transferred through the user's optic nerve). Some implementations, described herein, further provide a visual cortex monitoring system 220 that is capable of monitoring (and/or recording) brain activities resulting from photoacoustic-based stimulation, and providing closed-loop feedback that enables photoacoustic-based stimulation system 210 to calibrate photoacoustic-based stimulation parameters and adaptively operate for individual users.

In this way, the system(s) enable enhanced stimulation resolution and deeper penetration of neuronal cells, thus providing more effective virtual sensory functionality for users. For example, excitation of an absorptive element and/or the like (e.g., to cause thermal stimulation and/or vaporization-based stimulation of neuronal cells) can result in depolarization of neuronal cells in controlled spatiotemporal resolution, providing sensory perception to a user such that the user may visually and/or auditorily perceive an environment, be alleviated from pain (e.g., from disease and/or the like) (e.g., via inhibition(s) to C-fiber nerves), become manipulated to perform motor function(s) (e.g., via muscle nerve and/or motor cortex stimulation), and/or the like. In cases where system implementations described herein are applied to a user's retinal neurons, for example, the user can experience improved virtual vision—e.g., fast and fine resolution of vision, such as that at greater than 64 static pixels of information. In addition, non-invasive, and compact, system implementations described herein reduce or eliminate a need for patients to undergo sensory-related implant surgeries (e.g., to a retina and/or the like), thereby reducing treatment costs and improving user safety. Furthermore, the use of a laser-based photoacoustic-based stimulation system (that leverages laser light) permits fine control of light pulse durations and targeting of light energy, which provides a high degree of operative flexibility. Moreover, closed-loop feedback, provided by the visual cortex monitoring system, also enables adaptive stimulation (e.g., for users with different ocular anatomies), which maximizes the performance of the photoacoustic-based stimulation system, and improves user safety.

The foregoing disclosure provides illustration and description, but is not intended to be exhaustive or to limit the implementations to the precise form disclosed. Modifications and variations are possible in light of the above disclosure or may be acquired from practice of the implementations.

As used herein, the term component is intended to be broadly construed as hardware, firmware, or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, and/or the like.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of possible implementations. In fact, many of these features may be combined in ways not specifically recited in the claims and/or disclosed in the specification. Although each dependent claim listed below may directly depend on only one claim, the disclosure of possible implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the term "one" or similar language is used. Also, as used herein, the terms "has," "have," "having," and/or the like are intended to be open-ended terms. Further, the phrase "based on" is intended to mean "based, at least in part, on" unless explicitly stated otherwise.

What is claimed is:

1. A method, comprising:
   obtaining, by a device, information relating to an environment of a user;
   processing, by the device, the information to derive one or more signals representative of the information;
   generating, by the device, a laser beam based on the one or more signals; and
   outputting, by the device, the laser beam toward a portion of an absorptive element after generating the laser beam,
     the laser beam being focused on the portion of the absorptive element,
     the absorptive element being disposed over a portion of a retina of the user, and positioned proximate to a region-of-interest, of the user, that includes neuronal cells,
     the laser beam causing the absorptive element to produce, via photoacoustic effect, acoustic energy that causes depolarization of the neuronal cells in a controlled spatiotemporal resolution in the region-of-interest, and
     the depolarization of the neuronal cells enabling the user to visually and/or auditorily perceive the environment, be alleviated from pain, and/or be manipulated to perform a movement of a body part of the user.

2. The method of claim 1, wherein the information includes image information; and
   wherein the region-of-interest includes retinal tissue.

3. The method of claim 1, wherein the information includes image information; and
   wherein the region-of-interest includes tissue of a visual cortex region of a brain of the user.

4. The method of claim 1, wherein the information includes audio information; and
   wherein the region-of-interest includes tissue relating to hearing function.

5. The method of claim 1, wherein the acoustic energy includes ultrasound energy.

6. A device, comprising:
   an image capturing component configured to capture images of an environment of a user;
   a light projection system configured to output a laser beam toward a portion of an absorptive element,
     the light projection system including a laser source and an optical imager;
   one or more memories; and
   one or more processors, communicatively coupled to the one or more memories, configured to:
     process, in real-time, the images captured by the image capturing component to derive signals for controlling the laser source;
     provide the signals to the laser source to enable the laser source to generate the laser beam; and
     cause the optical imager to raster scan the laser beam to the absorptive element,
       the absorptive element being configured to be disposed over a portion of a retina the user, and positioned proximate to a region-of-interest, of the user, that includes neuronal cells,
       the laser beam causing the absorptive element to produce, via photoacoustic effect, acoustic energy that causes depolarization of the neuronal cells in a controlled spatiotemporal resolution in the region-of-interest, and
       the depolarization of the neuronal cells enabling the user to visually and/or auditorily perceive the environment, be alleviated from pain, and/or be manipulated to perform a movement of a body part of the user.

7. The device of claim 6, wherein the laser source and/or the optical imager is configured to be implanted within a cavity of an eye of the user; and
   wherein the region-of-interest includes retinal tissue.

8. The device of claim 6, wherein the optical imager includes a pair of galvanic mirrors and one or more microelectromechanical system (MEMS) actuators.

9. The device of claim 6, wherein the device is configured to be disposed entirely exterior to the user.

10. The device of claim 6, wherein the device is implemented in a glasses frame.

11. The device of claim 6, wherein the laser beam causes the absorptive element to undergo thermoelastic expansion.

12. The device of claim 6, wherein the absorptive element is composed of biocompatible material.

13. The device of claim 6, wherein the absorptive element includes a metamaterial structure.

14. The device of claim 13, wherein a physical property of the metamaterial structure is defined so as to prevent thermal damage to the neuronal cells.

15. The device of claim 6, wherein the absorptive element includes an anterior absorptive layer, a posterior absorptive layer, and a diced piezoelectric array disposed between the anterior absorptive layer and the posterior absorptive layer; and
   wherein the diced piezoelectric array is substantially transparent to light, and capable of generating an electric field, for stimulating the neuronal cells, based on acoustic energy provided by the anterior absorptive layer and the posterior absorptive layer.

16. The device of claim 6, wherein a first component of the absorptive element is configured to absorb a portion of the laser beam and a second component of the absorptive element is configured to pass through a remaining portion of the laser beam.

17. A non-transitory computer-readable medium storing instructions, the instructions comprising:
   one or more instructions that, when executed by one or more processors, cause the one or more processors to:

obtain information relating to an environment of a user;
process the information to derive one or more signals representative of the information;
generate a laser beam based on the one or more signals; and
output the laser beam toward a portion of an absorptive component after generating the laser beam,
    the laser beam being focused on the portion of the absorptive component,
    the absorptive component including:
        a first absorptive layer,
        a second absorptive layer, and
        a piezoelectric array disposed between the first absorptive layer and the second absorptive layer,
    the absorptive component being positioned over a portion of a retina of the user and proximate to a region-of-interest, of the user, associated with neuronal cells,
    the laser beam enabling the first absorptive layer and the second absorptive layer to produce, via photoacoustic effect, acoustic energy that activates the piezoelectric array to cause depolarization of the neuronal cells in a controlled spatiotemporal resolution in the region-of-interest,
        the depolarization of the neuronal cells enabling the user to visually and/or auditorily perceive the environment, be alleviated from pain, and/or be manipulated to perform a movement of a body part of the user.

18. The non-transitory computer-readable medium of claim 17, wherein the one or more instructions, when executed by the one or more processors, further cause the one or more processors to:
receive calibration data from a visual cortex monitoring system; and
adjust the laser beam based on the calibration data.

19. The non-transitory computer-readable medium of claim 17, wherein the absorptive component includes a clamping material that limits thermal expansion of the absorptive component to one axis of the absorptive component.

20. The non-transitory computer-readable medium of claim 17, wherein the absorptive component is composed of palladium-nanoparticle silicone (PdNS).

\* \* \* \* \*